(12) United States Patent
Sternby

(10) Patent No.: US 7,488,447 B2
(45) Date of Patent: Feb. 10, 2009

(54) METHOD AND AN APPARATUS FOR DETERMINING THE EFFICIENCY OF DIALYSIS

(75) Inventor: Jan Peter Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 240 days.

(21) Appl. No.: 10/533,251

(22) PCT Filed: Oct. 28, 2003

(86) PCT No.: PCT/SE03/01666

§ 371 (c)(1),
(2), (4) Date: Apr. 29, 2005

(87) PCT Pub. No.: WO2004/039436

PCT Pub. Date: May 13, 2004

(65) Prior Publication Data

US 2006/0116624 A1      Jun. 1, 2006

Related U.S. Application Data

(60) Provisional application No. 60/422,410, filed on Oct. 30, 2002.

(51) Int. Cl.
*A61M 1/36* (2006.01)
*A61M 37/00* (2006.01)
*C02F 1/44* (2006.01)

(52) U.S. Cl. .................. 422/44; 604/5.04; 604/5.01; 604/6.09; 210/645; 210/739

(58) Field of Classification Search .............. 604/4.01, 604/5.01, 5.04, 6.09, 6.11; 210/645, 646, 210/600, 633, 739, 944, 746, 203, 416.1, 210/433.1, 500.21; 422/44; 600/322; 436/178
See application file for complete search history.

(56) References Cited

U.S. PATENT DOCUMENTS

| | | | |
|---|---|---|---|
| 5,662,806 | A | 9/1997 | Keshaviah et al. |
| 5,685,988 | A | 11/1997 | Malchesky |
| 6,217,539 | B1 | 4/2001 | Goldau |
| 6,258,027 | B1 | 7/2001 | Sternby |
| 6,284,141 | B1 | 9/2001 | Shaldon et al. |

FOREIGN PATENT DOCUMENTS

| | | | |
|---|---|---|---|
| EP | 0 658 352 A1 | 6/1995 | |
| EP | 0 547 025 B1 | 6/1996 | |
| SE | 513 034 | 6/2000 | |
| WO | WO 98/55166 | * 12/1998 | |

* cited by examiner

*Primary Examiner*—Leslie R Deak
(74) *Attorney, Agent, or Firm*—Downs Rachlin Martin PLLC

(57) ABSTRACT

The invention relates to characterization of a dialyzer's capacity to accomplish a dialysis clearance of a patient, and strategies for improving the efficiency of a dialysis treatment of the patient The invention involves determining a whole body clearance ratio (420) for a dialysis treatment of a patient (410). The whole body clearance ratio expresses how well the patient responds to a potential cleaning capacity of a dialyzer, which is used to perform the treatment.

19 Claims, 21 Drawing Sheets

Definitions of clearance

◆ Dialyzer clearance     K    = removal rate / $C_b$
   (In vivo)
◆ Effective clearance   Keff = removal rate / $C_{mv}$
   (OnLine Clearance, Diascan)
◆ Whole body clearance  Kwb = removal rate / $C_{eq}$
   (Equilibrated clearance)

K > Keff > Kwb

Fig. 11

Measurement of effective clearance

◆ Through the effect of the dialyzer on a step in the inlet conductivity (Diascan)

◆ From the dialysate flow rate and the initial dialysate concentration together with the predialysis plasma water concentration

Fig. 12

METHOD AND AN APPARATUS FOR DETERMINING THE EFFICIENCY OF DIALYSIS

CROSS REFERENCE TO RELATED APPLICATION

This application is an national phase application based on PCT/SE2003/001666, filed Oct. 28, 2003, which claims the benefit of U.S. Provisional Application No. 60/422,410, filed Oct. 30, 2002, the content of both of which is incorporated herein by reference in its entirety.

THE BACKGROUND OF THE INVENTION AND PRIOR ART

The present invention relates generally to dialysis clearance. More particularly the invention relates to a method of estimating a process efficiency of a dialysis system according to the preamble of claim 1, a method of estimating a whole body clearance ratio according to the preamble of claim 6, corresponding computer programs and computer readable media according to claims 11 and 13 respective 12 and 14, an apparatus adapted to estimate a whole body clearance ratio according to claim 16, as well as use of this apparatus according to claim 17. The invention also relates to a method of performing a dialysis treatment program according to the preamble of claim 15.

Generally in dialysis, there is a large need to better understand the differences between patients, and what factors determine the achievable efficiency of the dialysis treatment in the individual patients. In theory, a number of different parameters may be used to characterize a dialyzer's capacity to filter waste products from a patient's bloodstream and restore the normal constituents of his/her blood. For example, models for solute concentrations in the different body parts may be used. It is also possible to characterize patients by measurable parameters, which in turn, may be used to improve the efficiency of the dialysis treatments.

A good model to use in order to understand the process of dialysis for cleaning the body from a solute is the so-called regional blood flow model for the solute distribution in the body, which was developed by Daugirdas and Schneditz. Urea is a common marker molecule for the description of the dialysis progress, and will be used for the following discussion for this purpose. However, the same discussion may also be applied to other solutes, such as creatinine, glucose, phosphate and other ions. According to one model, the human body includes two urea containing pools; one large pool of volume $V_L$, which is perfused by a relatively small blood flow $Q_L$, and one small pool of volume $V_H$, which is perfused by a relatively large blood flow $Q_H$, see FIG. 1. The small pool of volume $V_H$ represents the blood in the internal organs, such as the liver etc., and the large pool of volume $V_L$ represents blood located in the muscles, the skin and the like. Due to the comparatively large blood flow $Q_H$ to the small pool of volume $V_H$, this pool will be much more efficiently depurated than the large pool of volume $V_L$. Thus, after an initial transient, the concentration of urea $C_H$ in the small pool of volume $V_H$ will be lower than the concentration of urea $C_L$ in the large pool of volume $V_L$. Before returning to the heart η, the blood from the two pools $V_L$ and $V_H$ will be mixed, and a mixed venous urea concentration $C_{mv}$ therefore becomes a weighted mean value of the two pool concentrations $C_L$ and $C_H$, with the respective flow weights $Q_L$ and $Q_H$, according to the following:

$$C_{mv} = \frac{Q_L \cdot C_L + Q_H \cdot C_H}{Q_L + Q_H}$$

The denominator here represents the total blood flow $Q_L+Q_H$. Note that the mean value $C_{mv}$ falls between the two pool concentrations $C_L$ and $C_H$. However it will be closer to the concentration of urea $C_H$ in the small pool of volume $V_H$ because its weight $Q_H$ is larger than $Q_L$. Before reaching the heart η, the mixed venous blood will also mix with partly cleaned blood from the dialyzer 130, so that the concentration of urea in the heart η which is equal to a concentration $C_b$ returning to the access and the dialyzer, will be lower than all other concentrations.

When discussing the depuration of the whole body it is of interest to also discuss the mean concentration of urea in the whole body. This is sometimes referred to as the equilibrated concentration $C_{eq}$, since it is the concentration which would be the result if the body were left to equilibrate the pool concentrations $C_L$ and $C_H$. In our regional blood flow model, the equilibrated concentration $C_{eq}$ is:

$$C_{eq} = \frac{V_L \cdot C_L + V_H \cdot C_H}{V_L + V_H}$$

The equilibrated concentration $C_{eq}$ will also fall between the pool concentrations $C_L$ and $C_H$. However, it will be closer to the concentration of urea $C_L$ in the large pool of volume $V_L$ because of the volume $V_L$ being larger than the volume $V_H$. Consequently, we obtain the relationship:

$$C_L > C_{eq} > C_{mv} > C_H > C_b$$

Clearance is an entity which is used to describe the efficiency of the depuration process. More precisely, clearance is defined as the removal rate divided by the concentration of the substance in the fluid to be cleaned. Normally, a dialyzer clearance K, which is used to characterize dialyzers at different flow conditions, is defined as the removal rate divided by the concentration $C_b$, i.e. the concentration in the blood returning from the heart-lung system to the access and the dialyzer. A part of the cleaned blood from the dialyzer which is mixed with the blood returning from the body goes from the heart and enters directly into the dialyzer again. This is called cardiopulmonary recirculation, and is the reason why blood entering the dialyzer has a lower concentration (i.e. $C_b$) than the blood returning from the body. A so-called effective clearance $K_{eff}$ is instead defined as the removal rate divided by the mixed venous concentration $C_{mv}$, and is a better measure of the effective depuration of the patient. The effective clearance $K_{eff}$ can be estimated if the removal rate is measured either on the blood side or on the dialysate side of the dialyzer, and the mixed venous concentration (or the systemic blood concentration) $C_{mv}$ is measured by stopping the blood pump during an interval (say 1 minute) to let the effect of the cardiopulmonary recirculation disappear before a blood sample is drawn. Another simple method to estimate the effective clearance is to measure the effect in the outlet dialysate conductivity of a step in the inlet dialysate conductivity, for instance according to the procedures proposed in the documents EP 547 025, EP 658 352 and U.S. Pat. No. 6,217,539.

However, a still better measure would be to describe the cleaning of the whole body equilibrated concentration $C_{eq}$. This so-called whole body clearance $K_{wb}$ (or $K_{eq}$) is defined as the removal rate divided by the equilibrated concentration $C_{eq}$. Moreover, due to the relationships between the corresponding urea concentrations, we obtain the following relationships between the clearances:

$$K > K_{eff} \gg K_{eq}$$

Since it is relatively difficult to measure the pool concentrations $C_L$ and $C_H$ there is no straightforward way to measure the equilibrated concentration $C_{eq}$, and consequently, the whole body clearance $K_{wb}$ is also difficult to estimate. One possibility to measure the equilibrated concentration $C_{eq}$ is to wait until the concentrations have equilibrated after the treatment. However, this takes relatively long time (half an hour up to one hour) and is therefore impractical.

The interest in the whole body clearance $K_{wb}$ originates from the fact that this measure describes the cleaning effect of the dialyzer on the body, whereas the dialyzer clearance K and the effective clearance $K_{eff}$ constitute descriptions of the cleaning capacity of the dialyzer and the dialyzer together with the heart-lung system η and λ respectively. The dialyzer clearance K is known from the dialyzers data sheet, and the relationship between this measure and the effective clearance $K_{eff}$ is given by the expression:

$$K_{eff} = \frac{K}{1 + K/Q}$$

where Q is the total systemic blood flow, i.e. $Q = Q_L + Q_H$. Unfortunately, the relationship between the effective clearance $K_{eff}$ and the whole body clearance $K_{wb}$ is much less trivial.

It is nevertheless possible to study the theoretical relationship between the pool concentrations $C_L$ and $C_H$. Setting up a mass balance equation for each of the two pools of volume $V_L$ and $V_H$ leads to a system of two coupled first order differential equations for the concentrations $C_L$ and $C_H$. If we include the effect of a constant ultrafiltration rate, the pool volumes $V_L$ and $V_H$ will decrease linearly over time, and the differential equations for the concentrations $C_L$ and $C_H$ will have variable coefficients.

Daugirdas and Schneditz have managed to solve these equations for the case when the urea generation in the pool volumes $V_L$ and $V_H$ was included. Daugirdas and Schneditz studied the impact on the rebound of urea after treatment, i.e. the magnitude of the equilibration of urea concentrations after the treatment. However, the volumes $V_L$ and $V_H$ were allowed to vary, which in turn, led to a non-steady state relationship between the pool concentrations $C_L$ and $C_H$. Thus, a reliable estimate of the whole body clearance $K_{wb}$ could not be obtained.

The U.S. Pat. No. 6,258,027 discloses a method and a device for calculating dialysis efficiency with respect to a mass exchange of a solute in a fluid. However, no measure is determined which reflects the whole body clearance of the dialyzer on a patient.

SUMMARY OF THE INVENTION

The object of the present invention is therefore to alleviate the problems above and thus accomplish an improved estimation of the whole body clearance of the dialyzer on a particular patient and enabling identification of cases where an improvement is necessary, and probably possible.

According to one aspect of the invention, the object is achieved by the initially described method of estimating a process efficiency, wherein a whole body clearance ratio is determined, which expresses how well the patient responds to the potential cleaning capacity of a dialyzer.

An important advantage attained by this strategy is that the whole body clearance ratio provides an adequate measure of the actual usefulness of the dialysis treatment. Since each patient has his/her own characteristic response to a particular treatment, it is otherwise very difficult to determine the specific benefit of the dialysis process.

According to a preferred embodiment of this aspect of the invention, the whole body clearance ratio is determined by: measuring a final blood urea concentration, either immediately, or approximately one minute after the end of the treatment; measuring an equilibrated blood urea concentration no earlier than approximately one half hour to one hour after the end of the treatment; and dividing said final blood urea concentration by said equilibrated blood urea concentration. Thereby, a reliable measure is found, which reflects the process efficiency with respect to the patient.

According to another preferred embodiment of this aspect of the invention, the whole body clearance ratio is determined by: measuring an initial urea concentration; measuring, during the treatment at occasions being well spaced in time at least two subsequent urea concentration values after the treatment has started, a first value of said at least two values being measured no earlier than approximately one half hour after the treatment has started; deriving a starting urea concentration based on an extrapolation in time of said at least two values back to the start of the treatment; and dividing said starting urea concentration by said initial urea concentration.

According to yet another aspect of the invention, the object is achieved by the initially mentioned method of estimating the whole body clearance ratio of a dialysis treatment of a patient, wherein the whole body clearance ratio is determined on the basis of a measurement of a slope of a logarithmic removal rate function, which describes how a urea concentration is lowered in course of the treatment. This slope is namely a key factor in the whole body clearance ratio.

According to a first preferred alternative under this embodiment of the invention, the method involves the steps of: determining an initial dialysate urea concentration; determining a total flow rate value representing the spent dialysate during the treatment, including any ultrafiltration; calculating, based on measurements performed during a steady state phase of the treatment, the slope of the logarithmic removal rate function; measuring a predialysis urea mass in the patient; and determining the whole body clearance ratio as the product of the slope and the pre-dialysis urea mass, divided by the flow rate value and divided by the initial dialysate urea concentration.

According to a second preferred alternative under this embodiment of the invention, the method involves the steps of: calculating, based on measurements performed during a steady state phase of the treatment, the slope of said logarithmic removal rate function; determining an entire distribution volume; and determining the whole body clearance ratio as the product of said slope and said entire distribution volume divided by the potential cleaning capacity.

According to preferred embodiments of this aspect of the invention, the measurements relating to the slope of the logarithmic removal rate function may be performed either on a dialysate side or on a blood side of a dialysis system including the dialyzer and the patient.

According to a further aspect of the invention, the object is achieved by a computer program, which is directly loadable into the internal memory of a computer, and includes software for controlling the above proposed method when said program is run on a computer.

According to another aspect of the invention the object is achieved by a computer readable medium, having a program recorded thereon, where the program is to control a computer to perform the above-proposed method.

According to yet another aspect of the invention, the object is achieved by an apparatus, which is adapted to estimate the whole body clearance ratio of a dialysis treatment of a patient. Again, by efficiency is meant how well the patient responds to a cleaning capacity of a dialyzer, which performs the treatment. The apparatus includes a urea monitor and a processor. The urea monitor circuit is adapted to: determine an initial dialysate urea concentration; determine a total flow rate of spent dialysate during the treatment (including any ultrafiltration); during a steady state phase of the treatment, measure a slope of a logarithmic removal rate function, which describes how a dialysate urea concentration is lowered in course of the treatment; and measure a predialysis urea mass in the patient. The processor is adapted to determine the whole body clearance ratio of the patient by multiplying the slope of the logarithmic removal rate function with the predialysis urea mass and dividing the result thereof by the flow rate and the initial dialysate urea concentration. In similarity with the above-proposed method, this apparatus is advantageous because it provides a measure of the actual usefulness of the dialysis treatment.

According to yet another aspect of the invention, the object is achieved by using the above the apparatus for estimating the whole body clearance ratio of a dialysis treatment of a patient according to the proposed method.

A general advantage attained by the invention is that, based on the whole body clearance ratio for a dialysis treatment of a particular patient, a following treatment of the same patient can be made more efficient. Namely, if a relatively low ratio is determined, the next time, certain actions can be taken to improve the result of the dialysis. For instance, the treatment time can be prolonged, the composition of the dialysate can be altered, or some kind of intervention procedure with respect to the patient may be performed. The intervention procedure may involve subjecting the patient to physical exercise, massage, a change in the ambient temperature, an increased fluid intake, acupuncture, and/or medication affecting the systemic blood flow or the blood flow distribution in the patient's body.

BRIEF DESCRIPTION OF THE DRAWINGS

The present invention is now to be explained more closely by means of preferred embodiments, which are disclosed as examples, and with reference to the attached drawings.

FIGS. 7-24 illustrate dialysis examples which further elucidate the strategy according to the invention.

DESCRIPTION OF PREFERRED EMBODIMENTS OF THE INVENTION

Figure 1:
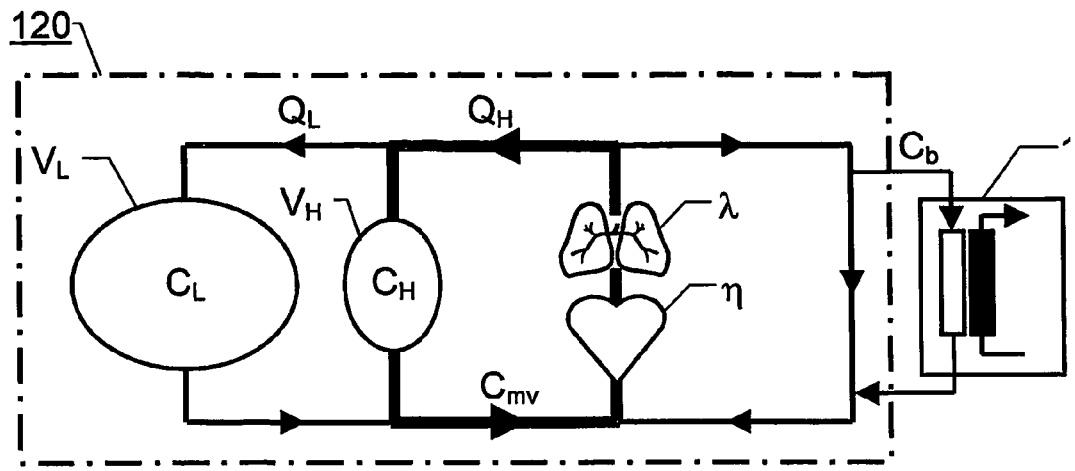
FIG. 1 shows a schematic model of a patient's bloodstream, which is connected to a dialyzer according to the invention.

Returning now to the FIG. 1, in contrast to Daugirdas and Schneditz, the invention presumes that the pool volumes $V_L$ and $V_H$ are constant. Thus, no ultrafiltration is presumed to take place, and the generation of urea is neglected. This means that it is possible to set up one differential equation for the ratio between the two pool concentrations $C_L$ and $C_H$. Moreover, it can be shown that the ratio between the two pool concentrations $C_L$ and $C_H$ tends towards a constant. This in turn, means that the clearance ratio: "whole body clearance"-to-"effective clearance" $K_{wb}/K_{eff}$ (which equals the ratio: "mixed venous concentration"-to-"equilibrated concentration" $C_{mv}/C_{eq}$) also tends towards a constant. The factors which determine the steady state ratios are the fraction of the large pool volume $V_L$ to the entire blood volume $V=V_L+V_H$, the fraction of the blood flow $Q_L$ in the large pool to the total systemic blood flow Q, and the fraction of the effective clearance $K_{eff}$ to the total systemic blood flow Q. Consequently, besides the effective clearance $K_{eff}$, the clearance ratio is only determined by patient specific parameters. All of the above is true if we relate the whole body clearance $K_{wb}$ to the dialyzer clearance K, instead of to the effective clearance $K_{eff}$. Normally, (for typical values) it takes approximately half an hour to one hour for a steady state level to be reached for these patient related parameters.

However, according to the invention, the ratio $K_{wb}/K_{eff}$ or $K_{wb}/K$ is used to characterize a dialyzer's capacity with respect to different patients. Provided that this is done at a specific K or $K_{eff}$ value, all the remaining parameters determining these ratios are patient specific, and may hence be used to specify how well the patient responds to the cleaning capacity of the dialyzer.

Figure 2:
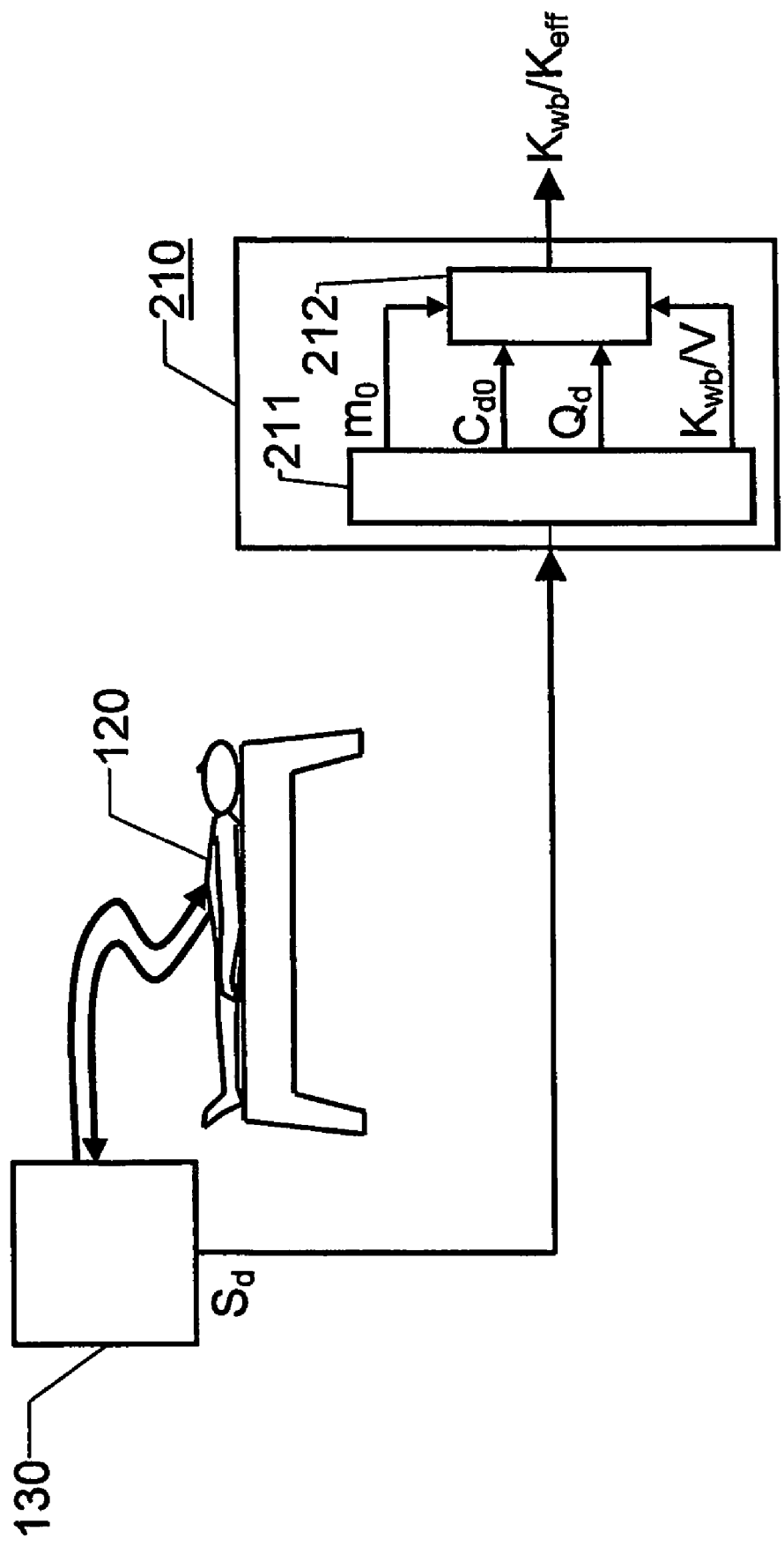
FIG. 2 illustrates a patient being attached to an apparatus for estimating a whole body clearance ratio of a dialysis treatment according to an embodiment of the invention.

FIG. 2 illustrates a situation where a patient 120 is connected to an apparatus 210 according to an embodiment of the invention. The apparatus 210 is adapted to estimate the efficiency (with respect to the whole body clearance ratio $K_{wb}/K_{eff}$) of a dialysis treatment of the patient 120 performed by a dialyzer 130.

The apparatus 210 includes a urea monitor circuit 211 and a processor 212. The urea monitor circuit 211 is adapted to measure a predialysis urea mass $m_0$ in the patient 120. The urea monitor circuit 211 is also adapted to determine an initial dialysate urea concentration $C_{d0}$ (e.g. by means of samples taken between $t_1$ and $t_2$ in FIG. 3, and an extrapolation back to zero) and a total flow rate $Q_d$ of spent dialysate during the treatment (including any ultrafiltration). During steady state phase of the treatment, the urea monitor circuit 211 measures a slope $K_{wb}/V$ of a logarithmic removal rate function, which describes how a dialysate urea concentration is lowered in course of the treatment (e.g. by means of samples taken between $t_3$ and $t_4$ in FIG. 3).

The processor 212 is adapted to determine the whole body clearance ratio $K_{wb}/K_{eff}$ for the patient 120 on the basis of the predialysis urea mass $m_0$, the slope $K_{wb}/V$ of the logarithmic removal rate function, the initial dialysate urea concentration $C_{d0}$ and the total flow rate $Q_d$. Specifically, the processor 212 calculates the whole body clearance ratio $K_{wb}/K_{eff}$ according to the expression:

$$\frac{K_{wb}}{K_{\textit{eff}}} = \frac{K_{wb}}{V} \cdot \frac{m_0}{Q_d \cdot C_{d0}}$$

i.e. the whole body clearance ratio $K_{wb}/K_{\textit{eff}}$ is determined as the product of the slope $K_{wb}/V$ and the predialysis urea mass $m_0$, divided by the flow rate $Q_d$ and the initial dialysate urea concentration $C_{d0}$.

The rationale behind this is that it is possible to calculate $K_{wb}/V$ as the slope of a logarithm curve, which describes the urea concentration in the spent dialysate. The urea concentration may be measured continuously by the urea monitor 211. These measurements also render it possible to determine the predialysis urea mass $m_0$, for example according to the procedure proposed in U.S. Pat. No. 6,258,027.

By definition, the predialysis urea mass $m_0$ equals the product of the distribution volume (i.e. the entire body water volume V in case of urea) and the plasma water concentration $C_{pw}$, i.e. $m_0 = V \cdot C_{pw}$. The plasma water concentration $C_{pw}$ may be measured in a blood sample drawn from the patient 120 before the treatment starts, and since the volume V is the volume of water. (with dissolved ions), the measured plasma concentration must be the plasma water concentration $C_{pw}$. An effective plasma water clearance, on the other hand, can be calculated from the removal rate and the plasma water concentration $C_{pw}$. This can be done at the start of the treatment.

However, the blood sample drawn from the patient before the treatment starts reflects an equilibrated (i.e. systemic) urea concentration. An effective clearance $K_{\textit{eff}}$ may therefore be calculated according to the expression:

$$K_{\textit{eff}} = \frac{Q_d \cdot C_{d0}}{C_{pw}}$$

where $Q_d$ is the flow rate of spent dialysate including any ultrafiltration, and $C_{d0}$ and $C_{pw}$ represent values of the initial dialysate urea concentration and the predialysis plasma water concentration respectively. Nevertheless, according to the invention, we are only interested in the ratio between $K_{wb}$ and $K_{\textit{eff}}$. Therefore, the plasma water concentration $C_{pw}$ can be eliminated, and no blood sample is required. Thus, provided that we know the dialysate flow rate $Q_d$, the clearance ratio $K_{wb}/K_{\textit{eff}}$ may be calculated by the processor 212 in the FIG. 2 as:

$$\frac{K_{wb}}{K_{\textit{eff}}} = \frac{K_{wb}}{V} \cdot \frac{m_0}{Q_d \cdot C_{d0}}$$

Figure 3:
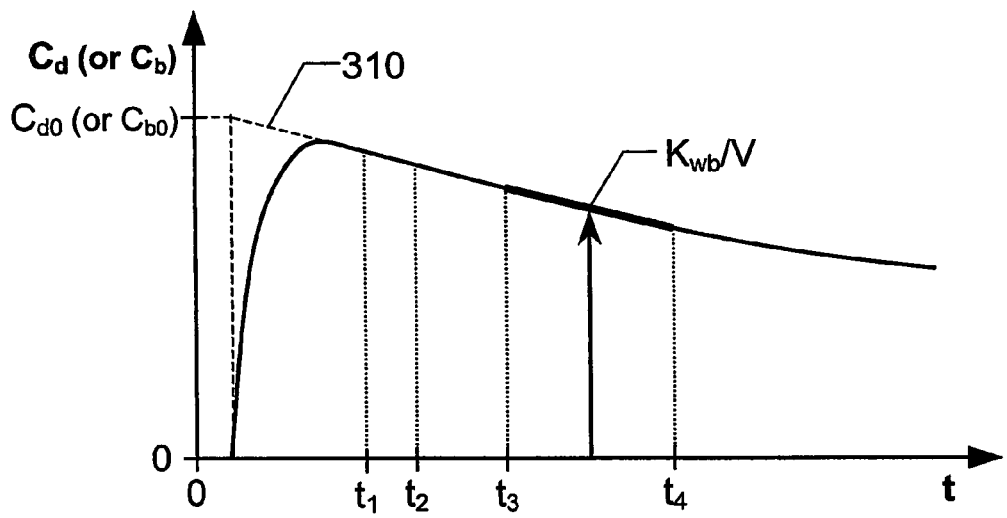
FIG. 3 is a graph over a removal rate function describing a first example of how a urea concentration is lowered during a dialysis treatment.

FIG. 3 is a graph over a removal rate function $C_d$ (or $C_b$) describing an example of how a urea concentration is lowered in the dialysate (or in the blood) during the dialysis treatment. In case the curve describes the dialysate urea concentration, an initial urea concentration $C_{d0}$ may be found from the urea curve in the urea monitor (see e.g. 211 in FIG. 2), by fitting an exponential 310 to the function during an initial phase of the treatment $t_1$ to $t_2$, say 5-20 minutes at the beginning of the treatment. Of course, a graph describing the removal rate function $C_b$ on the blood side actually starts at a non-zero initial urea concentration $C_{b0}$, at say twice the illustrated $C_{d0}$-value. However, this part of the graph is not shown here.

On the dialysate side, the exponential 310 is extrapolated backwards to the start (i.e. $t=0$) to find the initial dialysate urea concentration value $C_{d0}$. It generally takes about 5 minutes for the urea monitor 211 to find correct values at the start of the treatment, and this delay means that the dialysate urea $C_{d0}$ found by the proposed method is a value which corresponds to a fully developed cardiopulmonary recirculation. The initial blood urea concentration $C_{b0}$ is, on the other hand, most easily determined by means of a predialysis blood sample.

Figure 4:
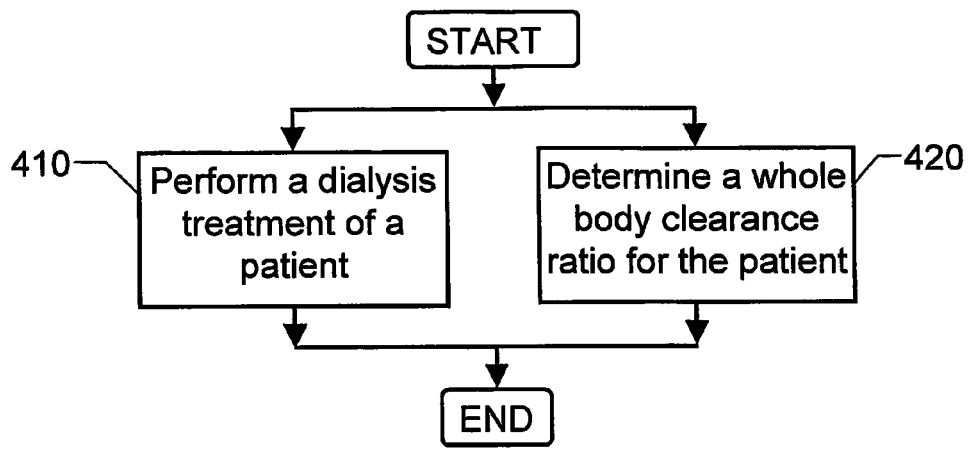
FIG. 4 shows a flow diagram which illustrates the general method of estimating a process efficiency of a dialysis system according to the invention.

FIG. 4 shows a flow diagram which illustrates the general method of estimating a process efficiency of a dialysis system according to the invention.

One step 410, involves performing a dialysis treatment of a specific patient. Another step 420, which is partly executed before and partly executed in parallel with the step 410, involves determining a whole body clearance ratio for the patient according to the above-proposed method. Although, of course, the dialysis treatment of the step 410 continues until the treatment is finished, the determination in the step 420 may be completed at an earlier point in time after which the procedure ends.

Figure 5:
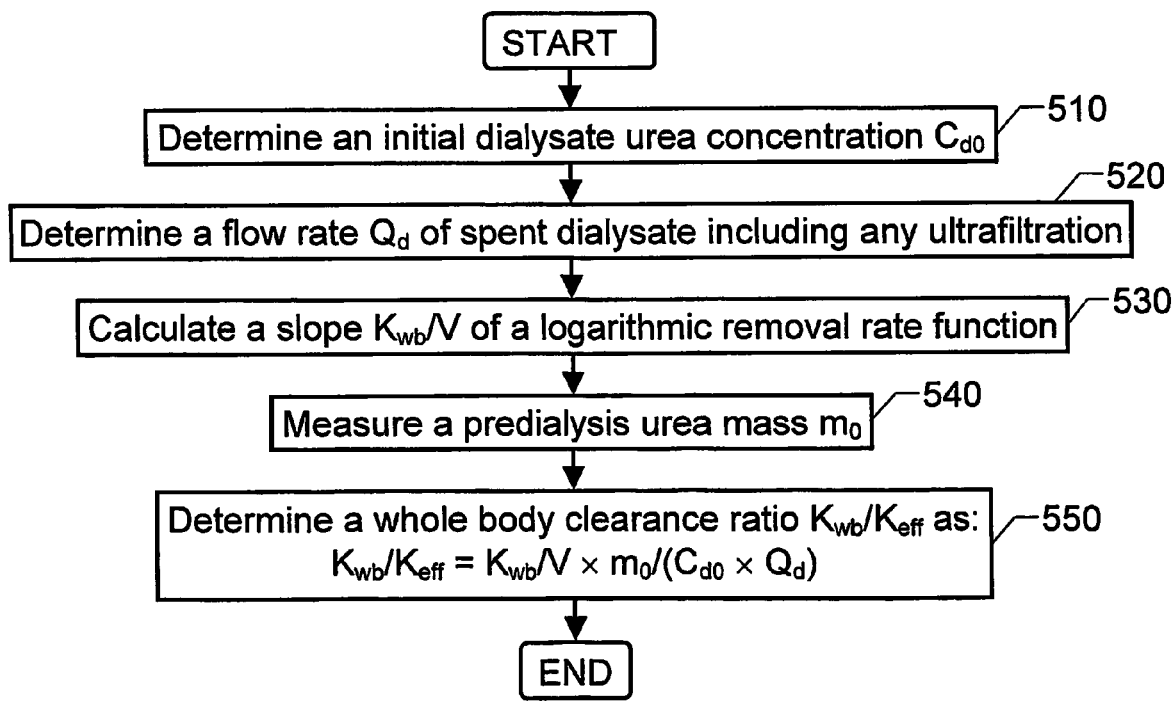
FIG. 5 shows a flow diagram which illustrates the general method of estimating a whole body clearance ratio of a dialysis treatment of a patient according to the invention, and FIG. 6 a graph over a removal rate function describing a second example of how a urea concentration is lowered during a dialysis treatment.

FIG. 5 shows a flow diagram which illustrates the general method of estimating a whole body clearance ratio of a dialysis treatment of a patient according to the invention.

A first step 510 determines an initial dialysate urea concentration $C_{d0}$. Then, a step 520 determines a total flow rate $Q_d$ of spent dialysate during the treatment, including any ultrafiltration. During a steady state phase of the treatment, measurements are performed reflecting the rate at which a dialysate urea concentration is lowered in course of the treatment. Specifically, a step 530 calculates a slope $K_{wb}/V$ of a logarithmic removal rate function, which describes the dialysate urea concentration over time. Subsequently, a step 540 determines a predialysis urea mass $m_0$ in the patient (for example according to the procedure proposed in U.S. Pat. No. 6,258,027). Finally, a step 550 determines the whole body clearance ratio $K_{wb}/K_{\textit{eff}}$ as the product of the slope $K_{wb}/V$ calculated in the step 530 and the predialysis urea mass $m_0$ (of the step 540), divided by the initial dialysate urea concentration $C_{d0}$ (determined in the step 510) and the flow rate $Q_d$ (determined in the step 520).

Returning now to FIG. 3, during a steady state phase of the treatment $t_3$ to $t_4$, say one hour or at least half an hour after the beginning of the treatment and onwards, a slope $K_{wb}/V$ of the logarithm of the dialysate concentration is calculated. As already mentioned above with reference to the FIG. 3, the slope $K_{wb}/V$ of the logarithm of the concentration may be measured on the dialysate side or on the blood side using at least two blood samples which are well spaced in time. The entire distribution volume V may be measured separately, and by multiplying the slope $K_{wb}/V$ with the volume V, the whole body clearance $K_{wb}$ can be obtained. The clearance ratio is then determined by dividing $K_{wb}$ by $K_{\textit{eff}}$ or K.

A straightforward way to measure the effective clearance $K_{\textit{eff}}$ or dialyzer clearance K is to register a removal rate (either on the blood side or on the dialysate side) and divide the registered figure by the systemic (or mixed blood venous) urea concentration $C_{mv}$ or dialyzer inlet concentration $C_b$ respectively.

Otherwise, the effective clearance $K_{\textit{eff}}$ may be measured by means of conductivity based methods, such as those described in the documents EP 547 025, EP 658 352 and U.S. Pat. No. 6,217,539. Alternatively, the dialyzer clearance K may be found from the dialyzer data sheet.

There are many ways to determine the entire distribution volume V. One possibility is to collect a part of the spent dialysate, from which removed urea is determined from the urea concentration multiplied by the total dialysate volume. After correction for urea generation, this measure is related to the change in the equilibrated blood urea concentration with a correction for ultrafiltration. The entire distribution volume V multiplied by the change in the corrected equilibrated blood concentration must equal the removed amount. This gives a value for the volume V.

Yet another possibility to obtain the clearance ratio is to measure the ratio between the final blood urea concentration shortly after the end of the treatment, and the equilibrated concentration $C_{eq}$ after half an hour to one hour, i.e. measure the urea rebound. If the final blood urea concentration directly after the end of the treatment is used, the figure reflects the ratio $K_{wb}/K$, since the effect of the cardiopulmonary recirculation will be included. If instead, a final blood urea concentration is used, which is measured about one minute after the end of the treatment, the figure reflects the ratio $K_{wb}/K_{eff}$ because then the effect of the cardiopulmonary recirculation has disappeared.

It should be noted that the actual equilibrated concentration $C_{eq}$ must be measured for the ratio calculation. For instance, it is not sufficient to calculate the equilibrated concentration $C_{eq}$ from the final concentration and the treatment efficiency (as suggested by Daugirdas), or to measure the concentration about 35 minutes before the end of the treatment (as suggested by Tattersall). Namely, these strategies will only provide a mean effect over a plurality of patients, not the effect with respect to each particular patient.

Another possibility is to study the urea concentration in the spent dialysate. This concentration shows a two-pool behavior. After the initial half hour to one hour the concentration follows a single exponential, whereas a first part of the curve is better described as a sum of this exponential and another exponential (which fades away more rapidly). Hence, these two exponentials may be used to characterize the patient with respect to the clearance ratio.

Figure 6:
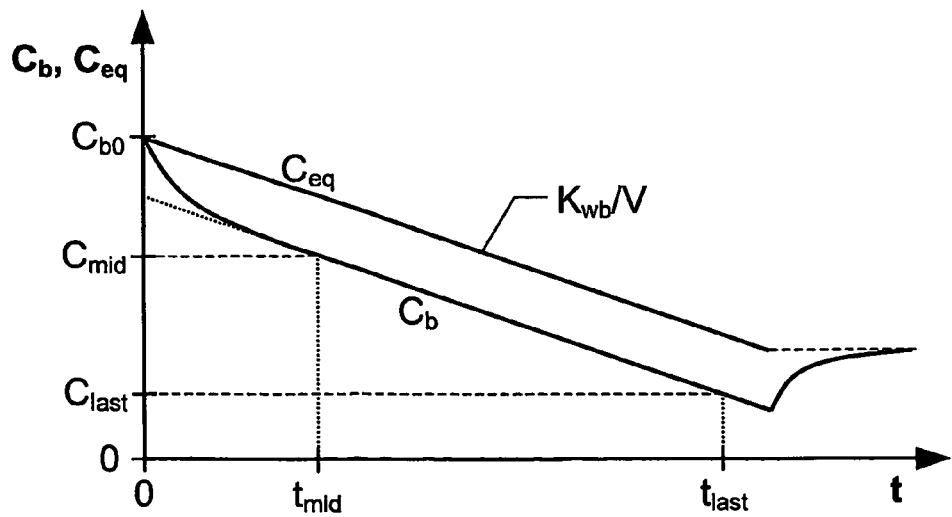

Referring to FIG. 6, an alternative to the above-described methods is to calculate the clearance ratio $K_{wb}/K$ from concentrations in three blood samples. A first sample $C_{b0}$ is taken just at the start of the treatment (i.e. t=0). A second sample $C_{mid}$ is taken at $t_{mid}$, at least half an hour to an hour into the treatment, after the gradient between the two body pools has developed. A third and final sample $C_{last}$ is taken at $t_{last}$ towards the end of the treatment. The logarithm of the two values $C_{mid}$ and $C_{last}$ are used to extrapolate linearly backwards to the start of the treatment in order to find what the initial concentration would have been if the gradient between the body pools had been fully developed already at the start. This value is then divided by the actual initial value obtained from the first sample $C_{b0}$ to find the clearance ratio $K_{wb}/K$. Consequently, the clearance ratio $K_{wb}/K$ is calculated as:

$$\frac{K_{wb}}{K} = \frac{C_b}{C_{eq}} = \frac{C_{last}}{C_{b0}} \cdot \left(\frac{C_{mid}}{C_{last}}\right)^{\frac{t_{last}}{t_{last}-t_{mid}}}$$

Below follows examples, which further elucidate the invention, by studying the relation between whole body clearance and effective blood water clearance for urea. Effective blood water clearance can be measured through the dialyzer effect on a step in the inlet conductivity. It is called effective because it takes into account the effect of recirculation, both cardiopulmonary and in the access. This has led to the misconception that this clearance also describes the total cleaning effect of the dialysis treatment. The differences between the two clearance definitions are important for dose calculations, and can also be used to explain differences between patients. To continue, we need to discuss the clearance definitions, and we will use the regional blood flow model for this purpose. The examples are described with reference to FIGS. 7 to 24.

Figure 7:
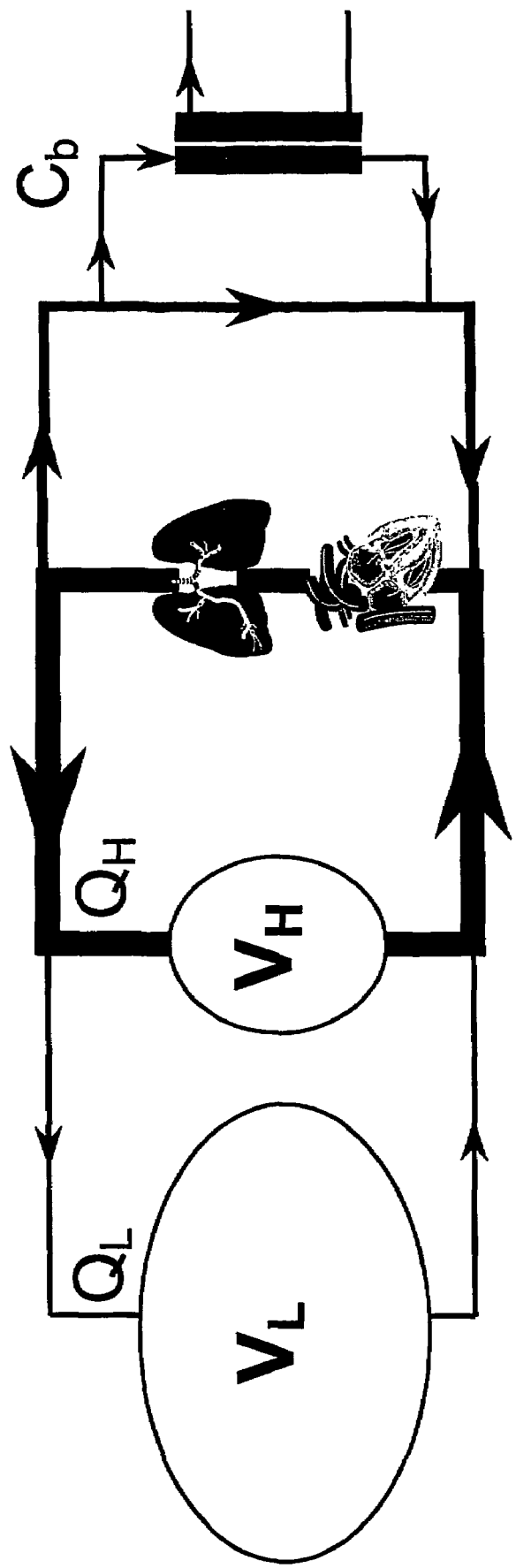

As shown in FIG. 7, in this model we have one small pool of volume $V_H$, corresponding to internal organs that are perfused by a high rate blood flow $Q_H$. The large pool with volume $V_L$ is perfused by the low rate blood flow $Q_L$. The heart-lung system is lumped together, and blood with a urea concentration $C_b$ enters the dialyzer.

Figure 8:
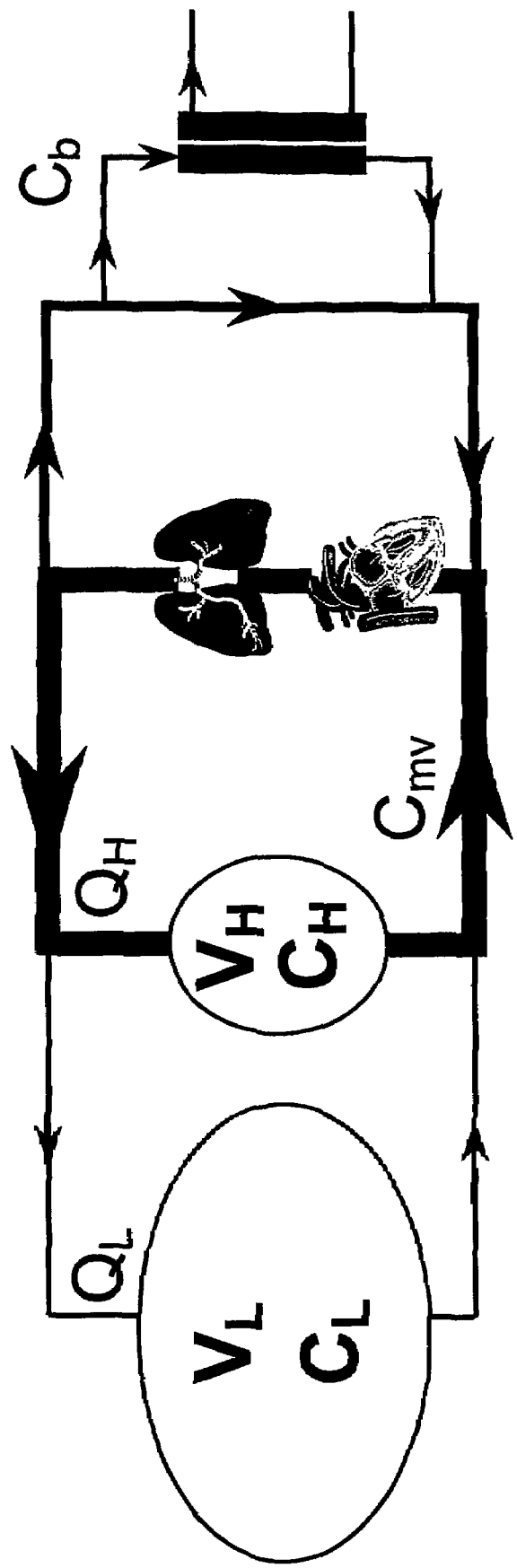

Referring now to FIG. 8, since the high flow pool will be more effectively cleaned, its concentration $C_H$ will always be lower than the low flow pool concentration $C_L$. The mixed venous concentration $C_{mv}$ coming back to the heart-lung system from the body is a result of the two pool concentrations being weighted together according to the flows $Q_H$ and $Q_L$. $C_{mv}$ must therefore lie in between $C_H$ and $C_L$, and it will be closer to $C_H$ because of the heavier weight from the high flow $Q_H$.

Figure 9:
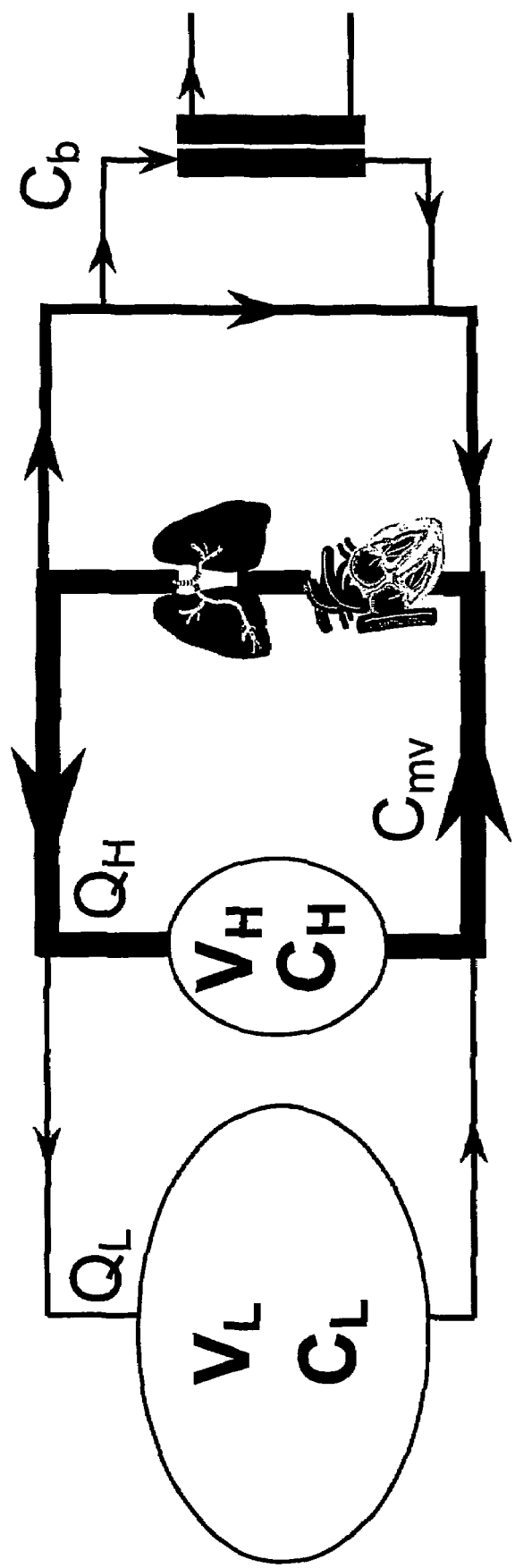

As depicted in FIG. 9, in order to measure the depuration of the whole body the equilibrated concentration $C_{eq}$ is more relevant than $C_{mv}$. $C_{eq}$ is also a weighted mean value of the pool concentrations, but with their volumes as weighting factors, which makes a big difference. Just as $C_{mv}$, $C_{eq}$ will also fall in between $C_H$ and $C_L$, but it will be closer to $C_L$ because of the heavier weight from the large low flow pool volume $V_L$.

Figure 10:
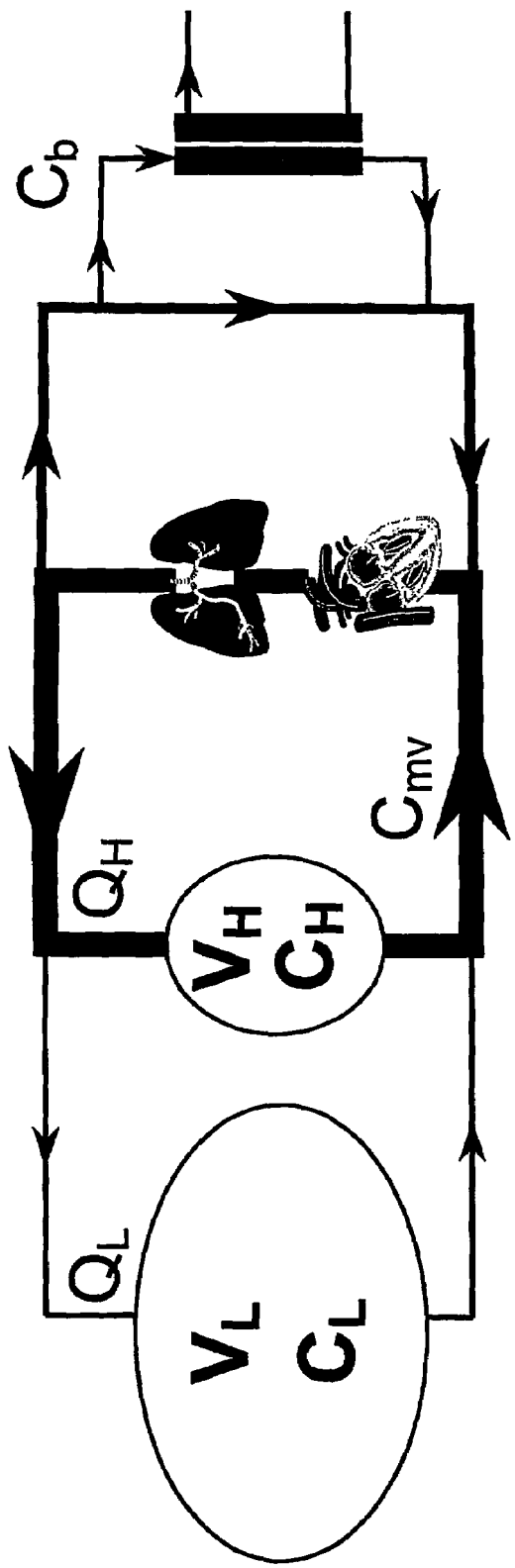

Then, in FIG. 10, we have this order between the different concentrations, with $C_b$ lowest as a result of mixing $C_{mv}$ with cleaned blood from the dialyzer. Since clearance is removal rate divided by concentration, we could have five different clearance values. $C_H$ and $C_L$ are of course less interesting, but the other three all have meaningful interpretations.

As defined in FIG. 11, the first one, which involves the blood concentration entering the dialyzer, is the normal dialyzer clearance that is used to characterize different dialyzers. If we use the mixed venous concentration we get the effective clearance, which will include the effects of both cardiopulmonary and access recirculation. This can be measured by conductivity methods such as OnLine Clearance from Fresenius and Diascan from Gambro. Finally we have the whole body clearance, which can also be called equilibrated clearance, and results if we use the equilibrated concentration. Because of the relation between the concentrations, we will always have this relation between the clearances, and our aim was to study the relation between the two last ones, both clinically and theoretically. So, how did we measure these clearances?

In FIG. 12, the effective clearance $K_{eff}$ was measured in two different ways.

Figure 13:
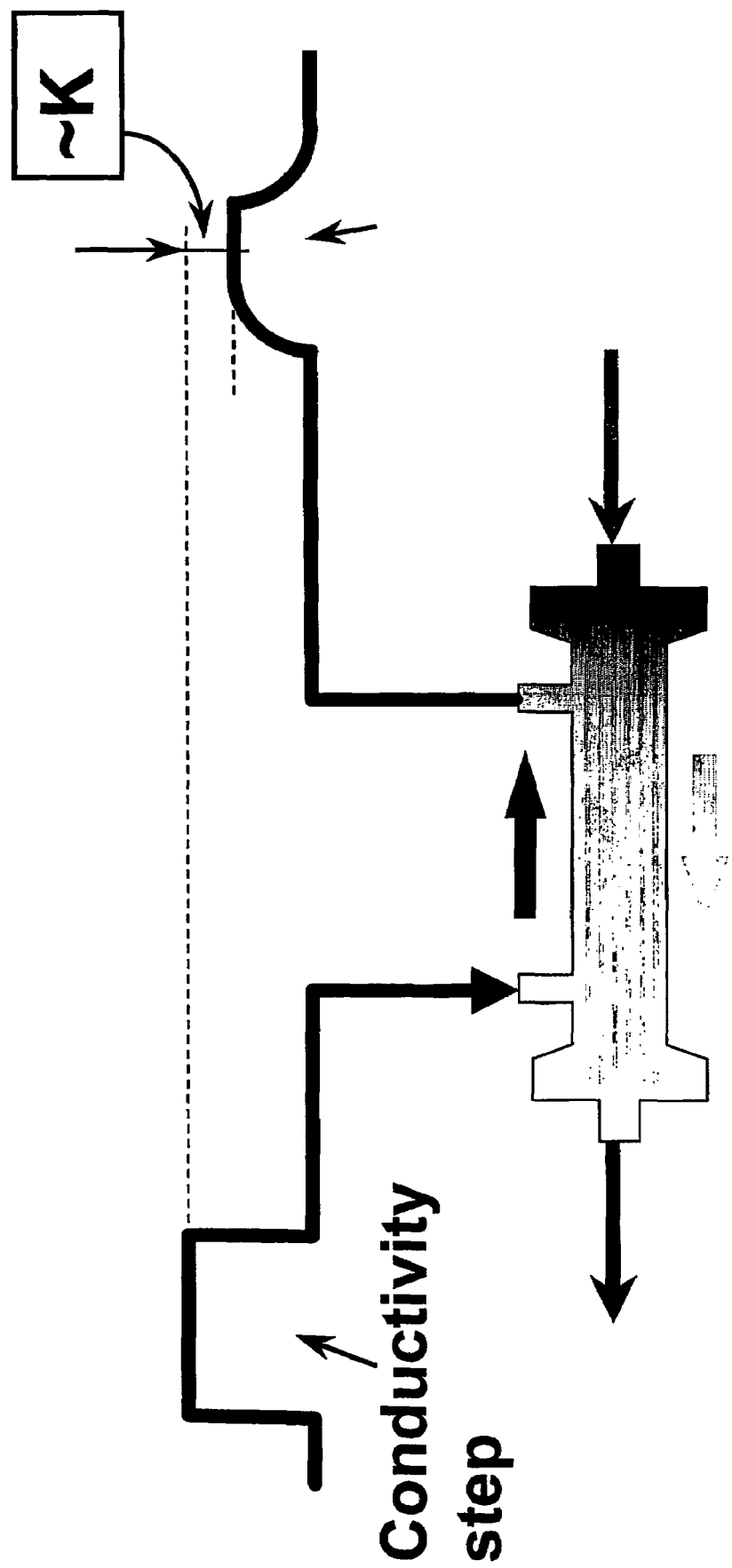

FIG. 13 presents clearance by conductivity. Firstly, using a step in the inlet conductivity of the dialysis fluid, clearance was calculated in the Integra dialysis machine from the decrease in the dialyzer of the conductivity step size. This is known to give an estimate of the effective plasma water clearance.

Figure 14:
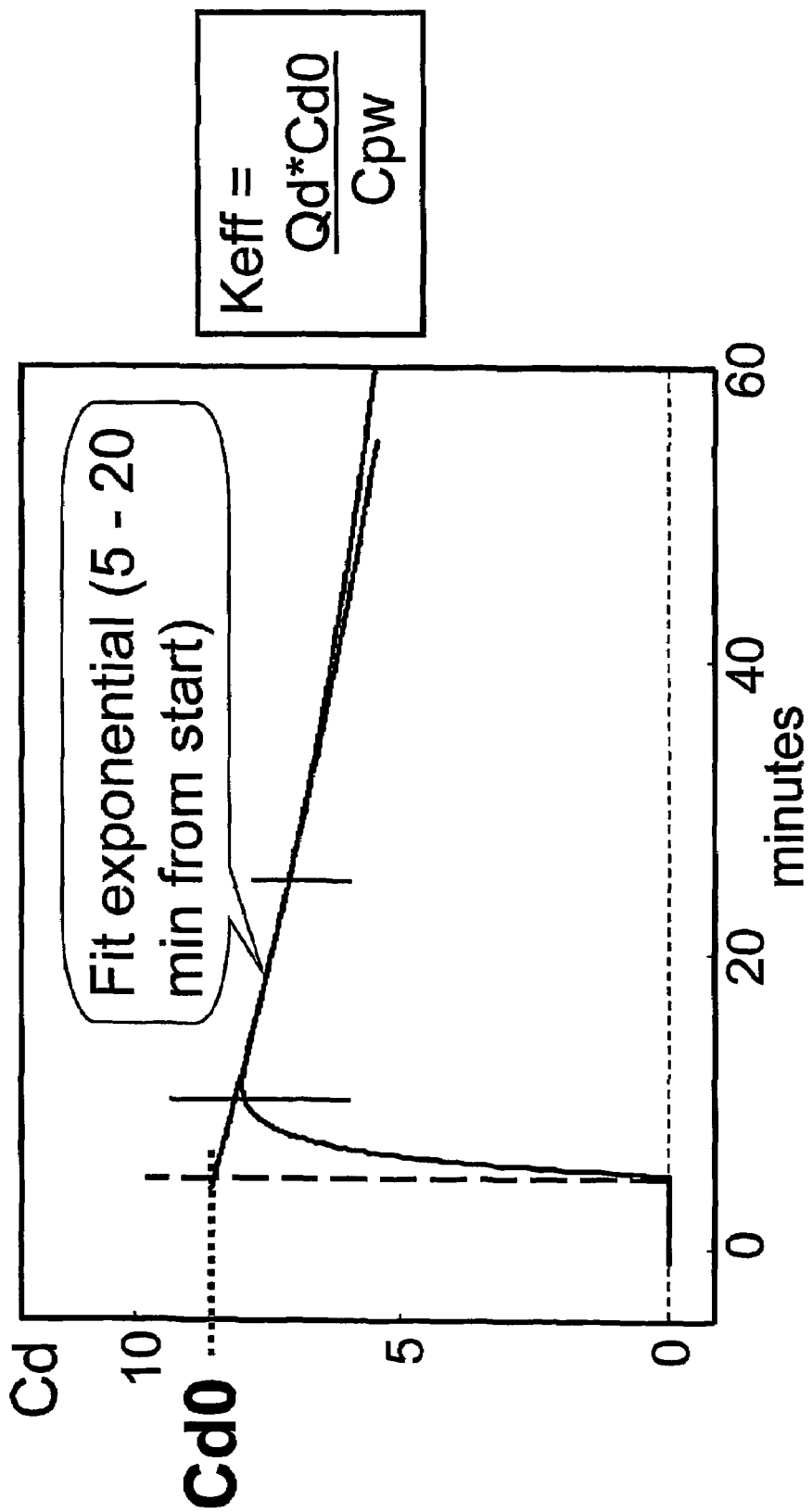

Secondly, as shown in FIG. 14, clearance was calculated from the dialysate flow rate and the initial urea concentrations in the dialysate and in plasma water. The dialysate concentration was measured continuously in the spent dialysate by a urea monitor.

The initial concentration was determined by fitting an exponential 5-20 minutes from the start, which was then extrapolated backwards. This calculation will give the effective clearance since the dialysate concentration after 5 minutes will refer to a fully developed cardiopulmonary recirculation, whereas the pretreatment blood sample gives the systemic blood urea concentration.

Figure 15:
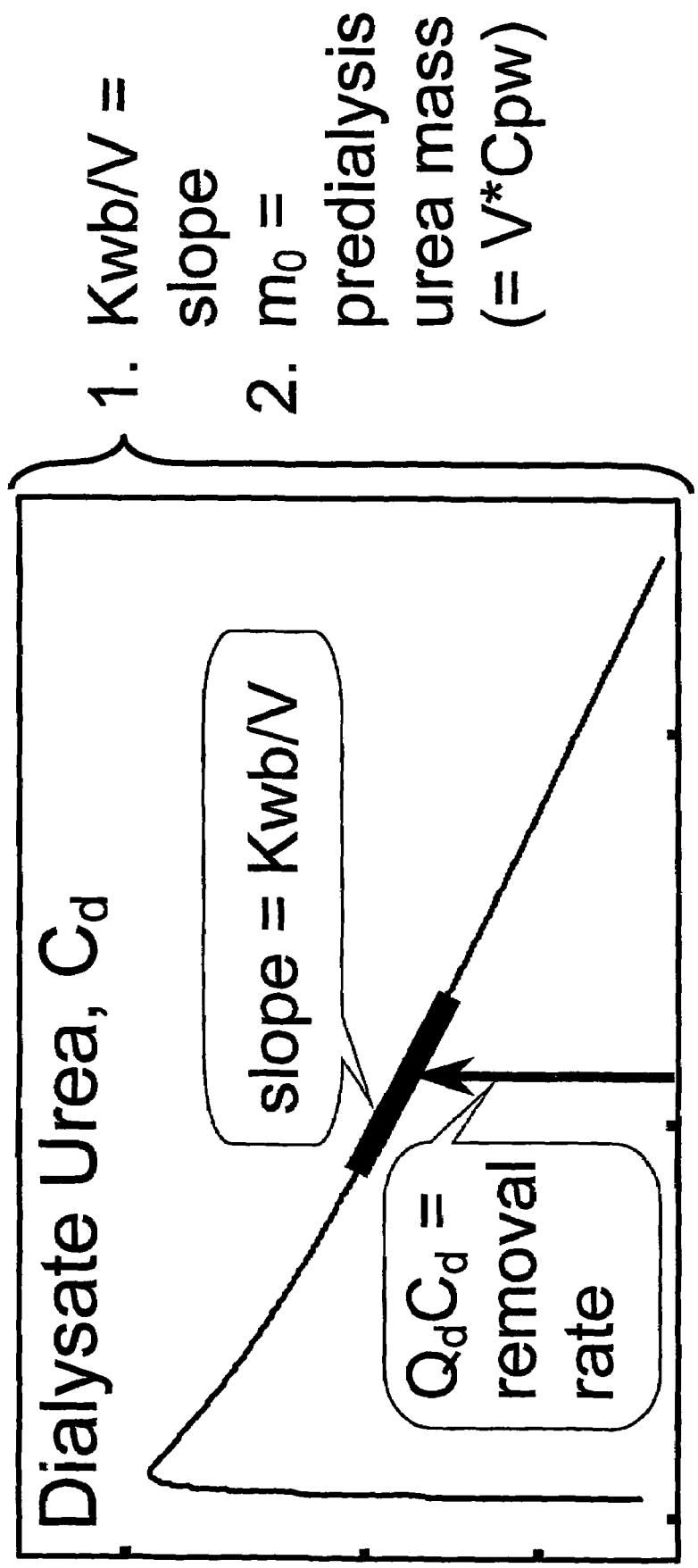

Then, shown in FIG. 15, the whole body urea clearance is obtained from the mass based urea kinetics that have been described elsewhere. This is a logarithmic plot of dialysate urea, and the negative steady state slope will be whole body K/V. From the slope and the removal rate it is possible to calculate mo, the predialysis urea mass in the body, and by definition this is equal to the product of volume and plasma water concentration. (Whole body Kt/V has been shown to agree with equilibrated Kt/V, and the volume V with volume determined by dialysate collection and DDQ, Direct Dialysate Quantification.)

Figure 16:
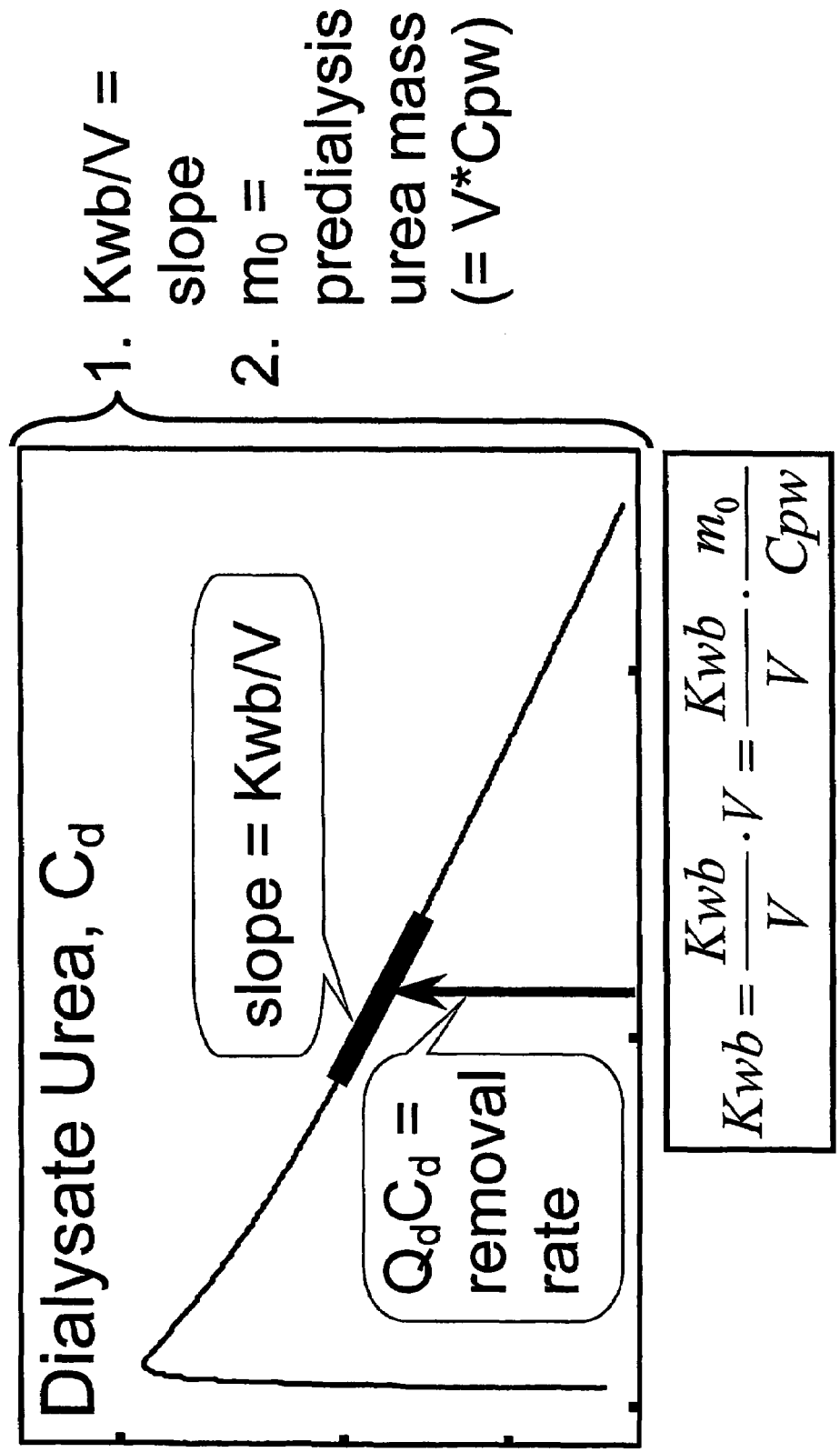

Also, as in FIG. 16, the whole body clearance can then be calculated as the product of the slope and the urea mass, divided by the plasma water concentration.

Figure 17:
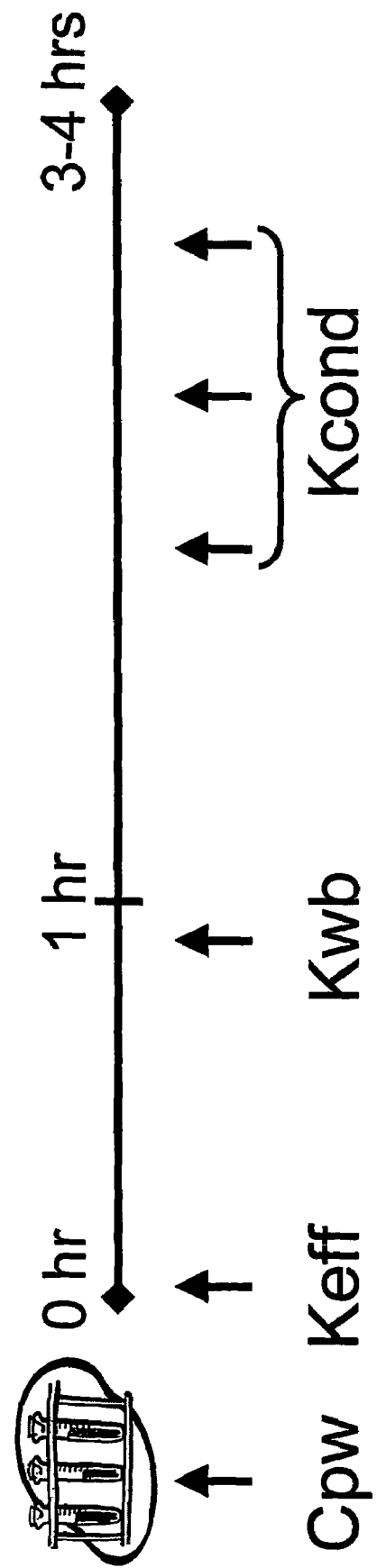

Then, in particular as shown in FIG. 17, we studied the relation between whole body clearance and effective clearance in 80 treatments of 20 patients. A urea monitor in the spent dialysate was used to calculate whole body clearance about one hour into the treatment. An Integra machine was used for 42 treatments and a Cobe C3 machine for the remaining 38. Effective clearance was calculated from the initial concentrations, but the conductivity-based clearance could be measured only in the Integra treatments. 9 treatments had to be discarded due to fistula recirculation or technical problems.

Figure 18:
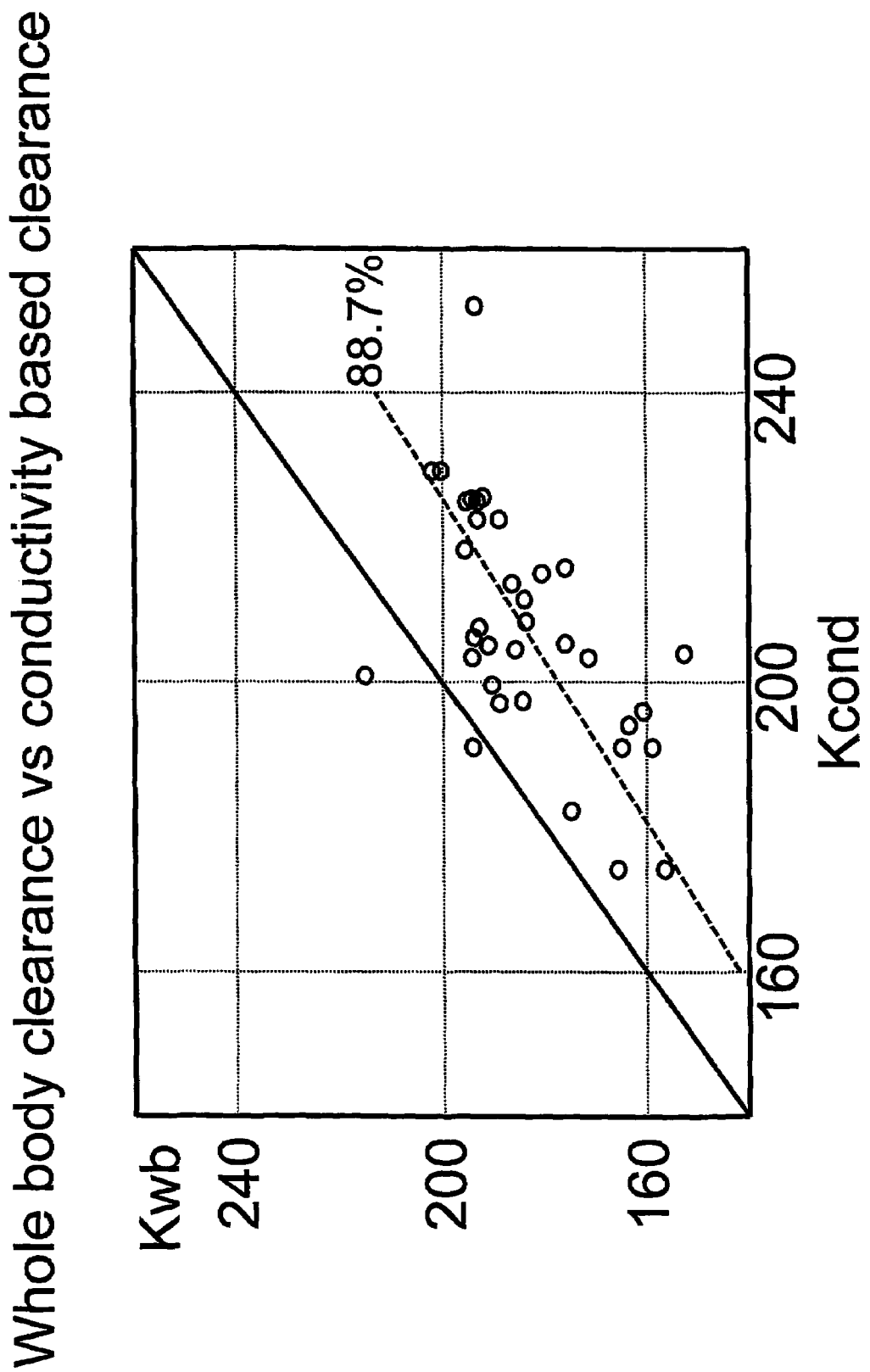

With reference to FIG. 18, we see a graph over the 35 remaining Integra treatments, where the whole body clearance is about 11% lower than the conductivity based clearance. But the data are fairly scattered, and we would therefore like to compare the whole body clearance with the initial effective clearance based on urea concentrations instead.

Figure 19:
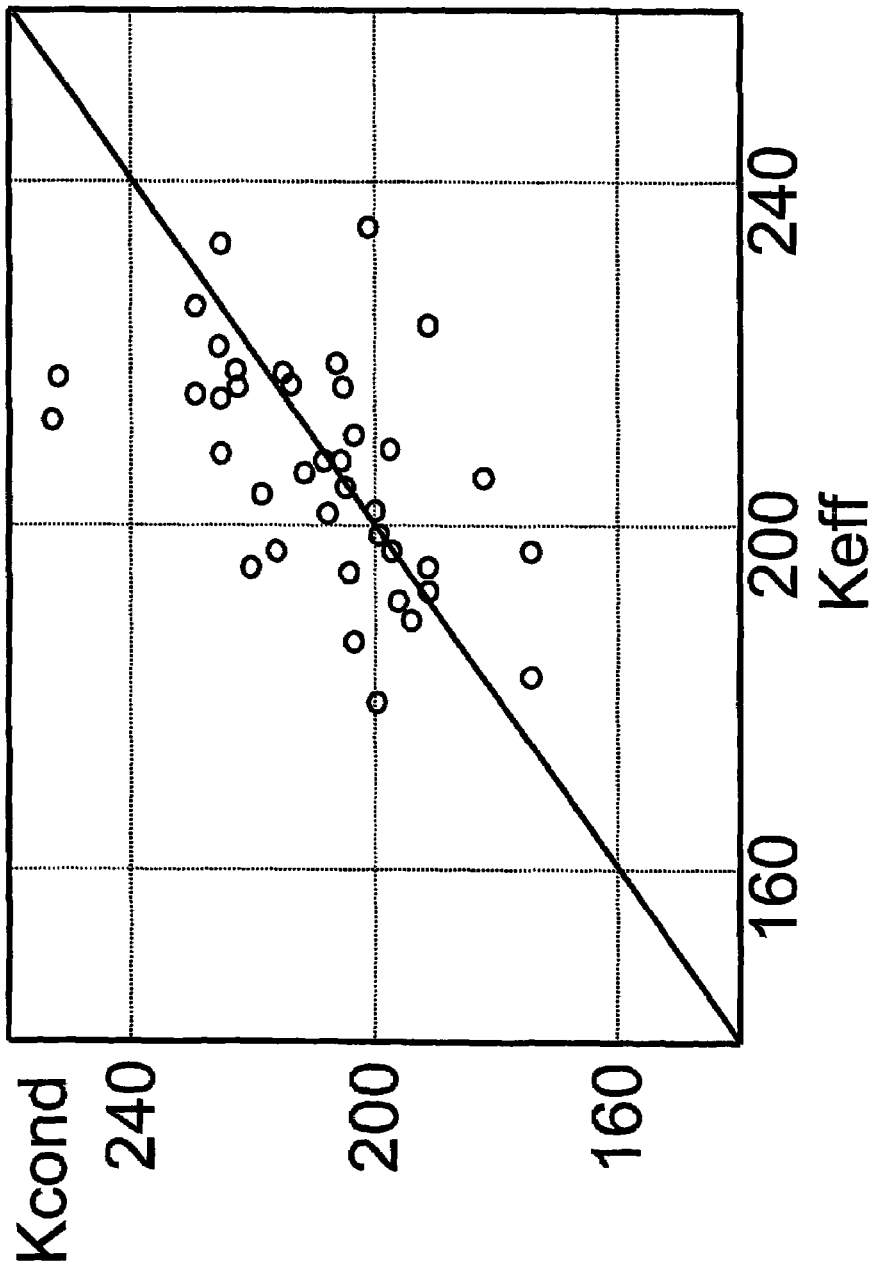

As shown in FIG. 19, this can be done since conductivity based clearance and initial effective clearance agree quite well as shown in this diagram from our study. This agreement has also been shown by several previous studies.

Figure 20:
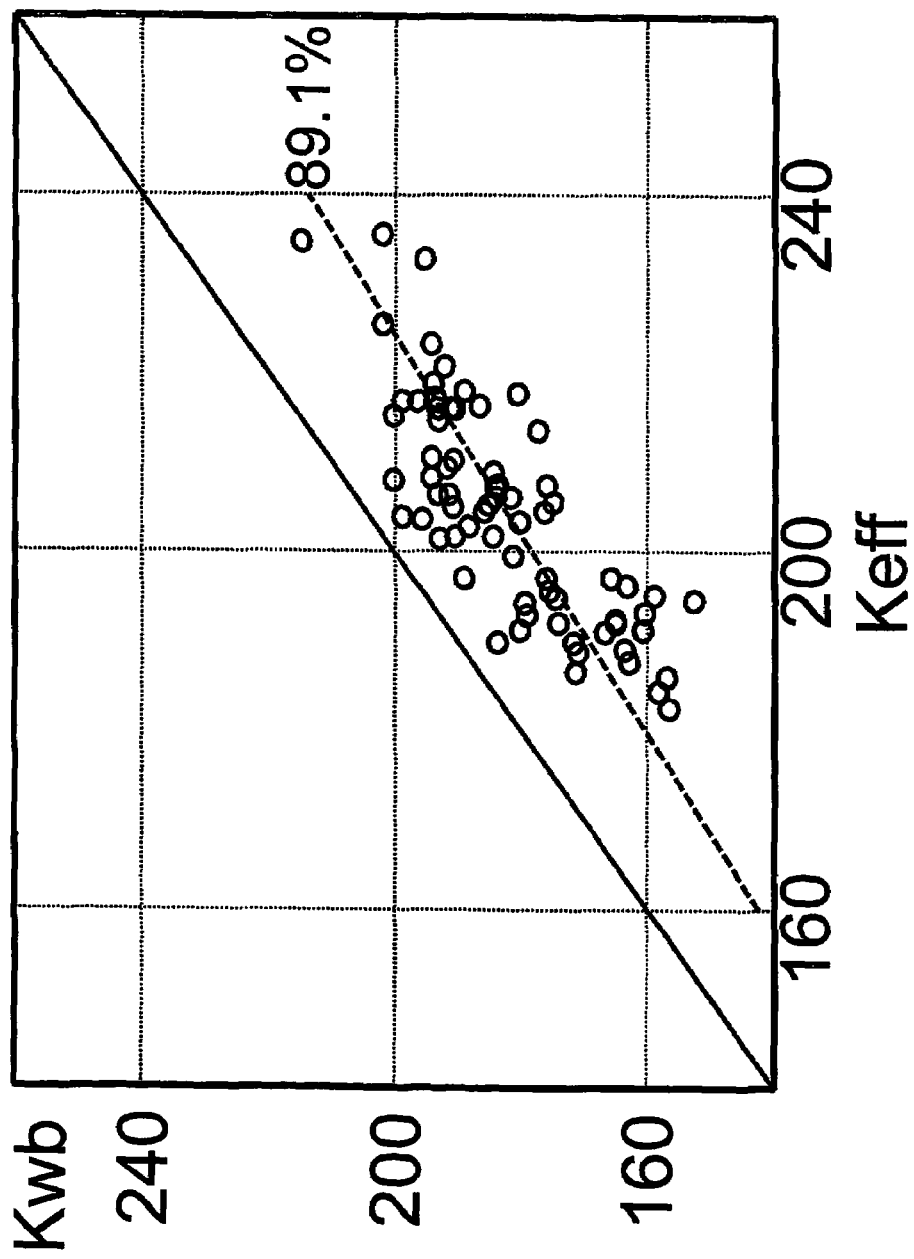

Referring to FIG. 20, if we now compare the whole body clearance to initial effective clearance based on urea concentrations in all remaining 71 treatments we see that the data are much less scattered. The difference is still about 11%. The next figure shows the ratio between these two clearances.

Figure 21:
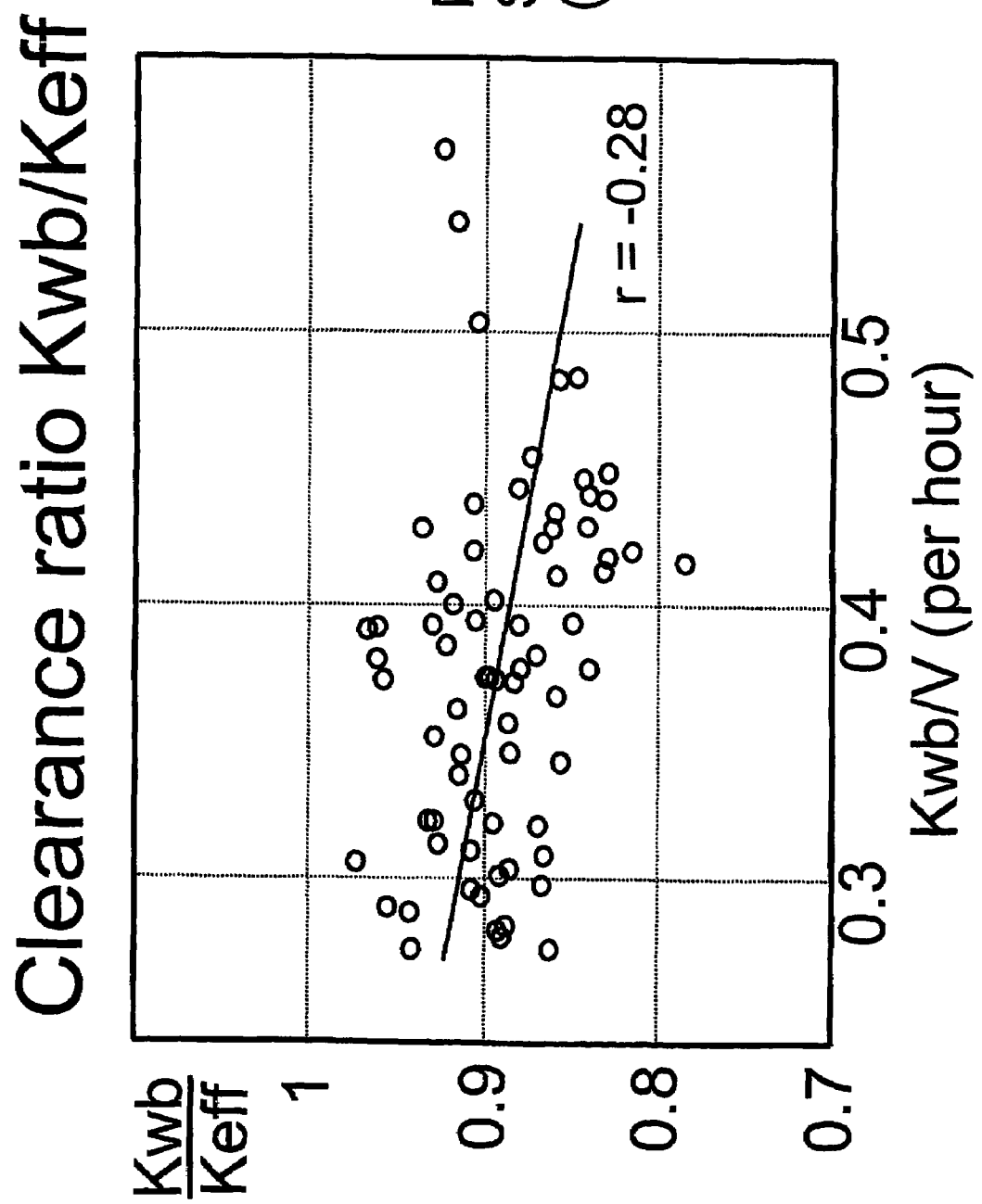

Then in FIG. 21, the ratio is shown as a function of the relative treatment efficiency, whole body K/V, and we see that there is a negative correlation. This corresponds to the correlation between K/V and the error in single pool Kt/V that is the basis for Daugirdas' rate equation.

Figure 22:
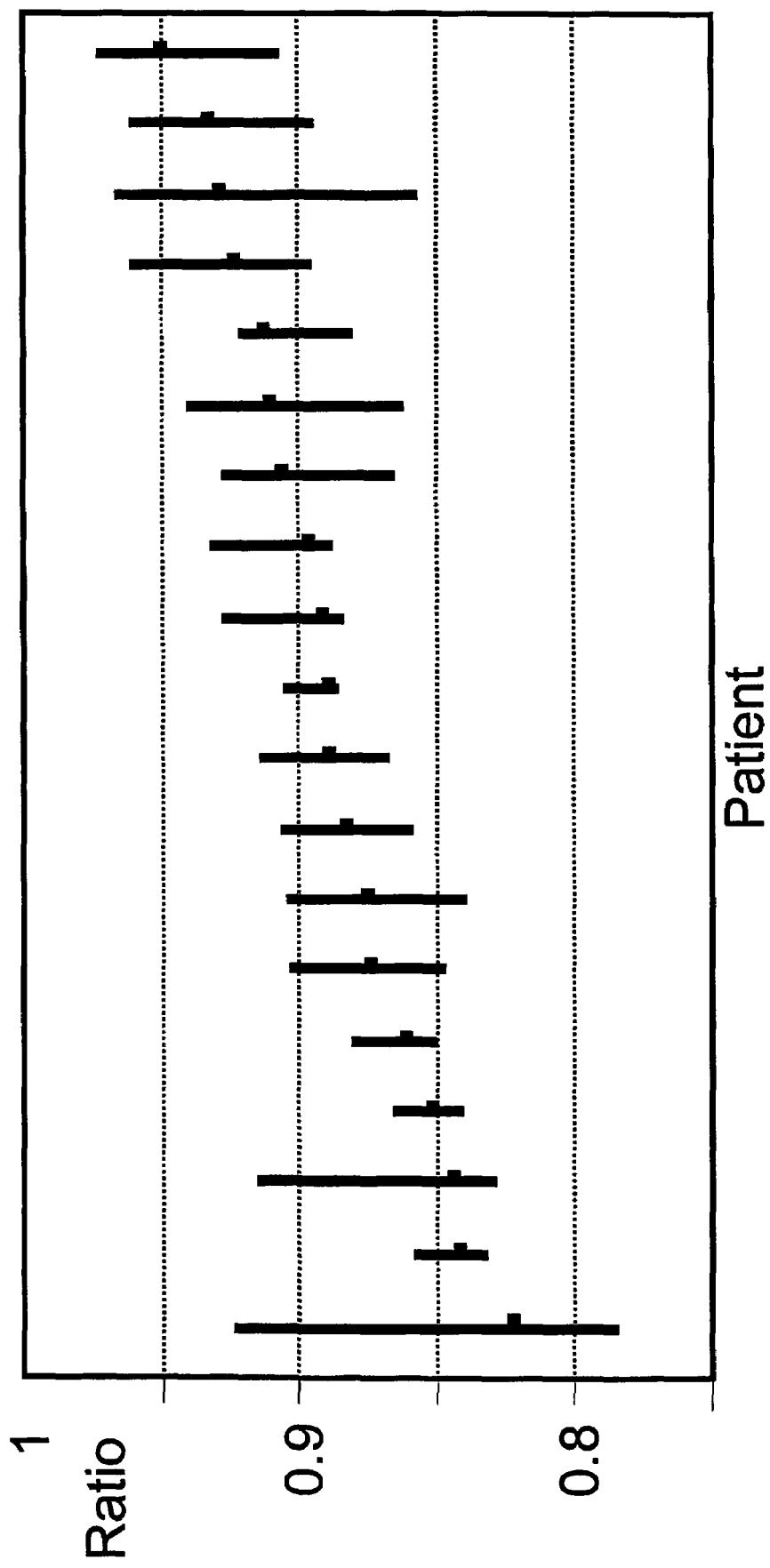

Next, in FIG. 22, if we look at the clearance ratios for each patient, we see that there is a clear difference between patients. Shown here are the range and median value for each patient, and the patients have been ordered according to median value. We see that the clearance ratio varies between roughly 0.8 and 0.95. For most patients the variation in ratio is less than the interpatient variation.

Figure 23:
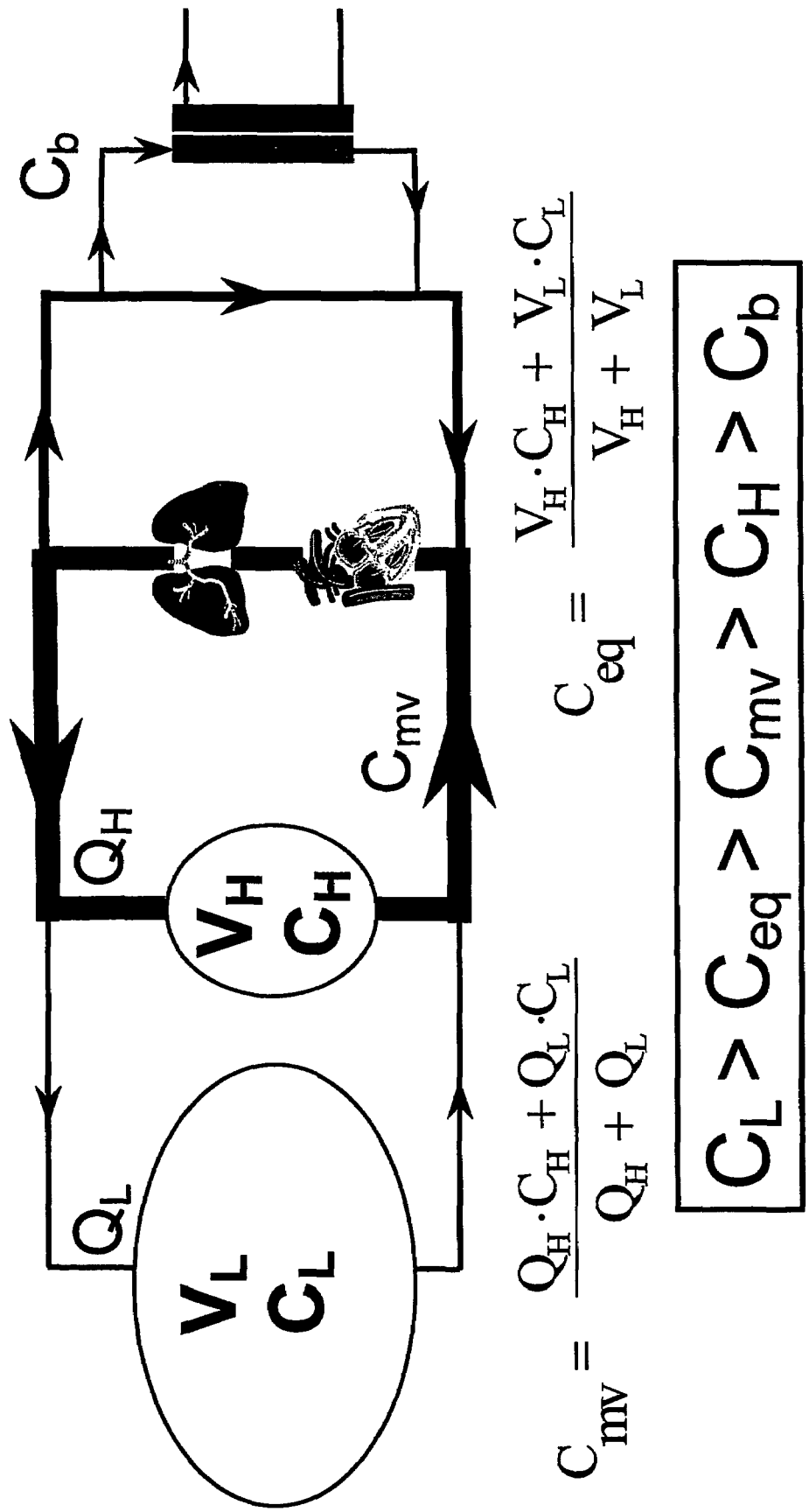

Referring now to FIG. 23, let us now go back and try to explain a theoretical basis for the ratio variations. Again the two-pool regional blood flow model will be used, and in the simplified analysis it is assumed that there is no ultrafiltration or urea generation. It is then possible to set up a differential equation describing the evolution of the ratio of the two pool concentrations, which shows that their ratio will fairly quickly approach a steady state value. This is all that is needed to calculate the steady state ratio between whole body clearance and effective clearance. The clearance ratio will depend on the ratio of the two volumes, the ratio of the two flows, and the ratio of the effective clearance to the systemic blood flow.

Figure 24:
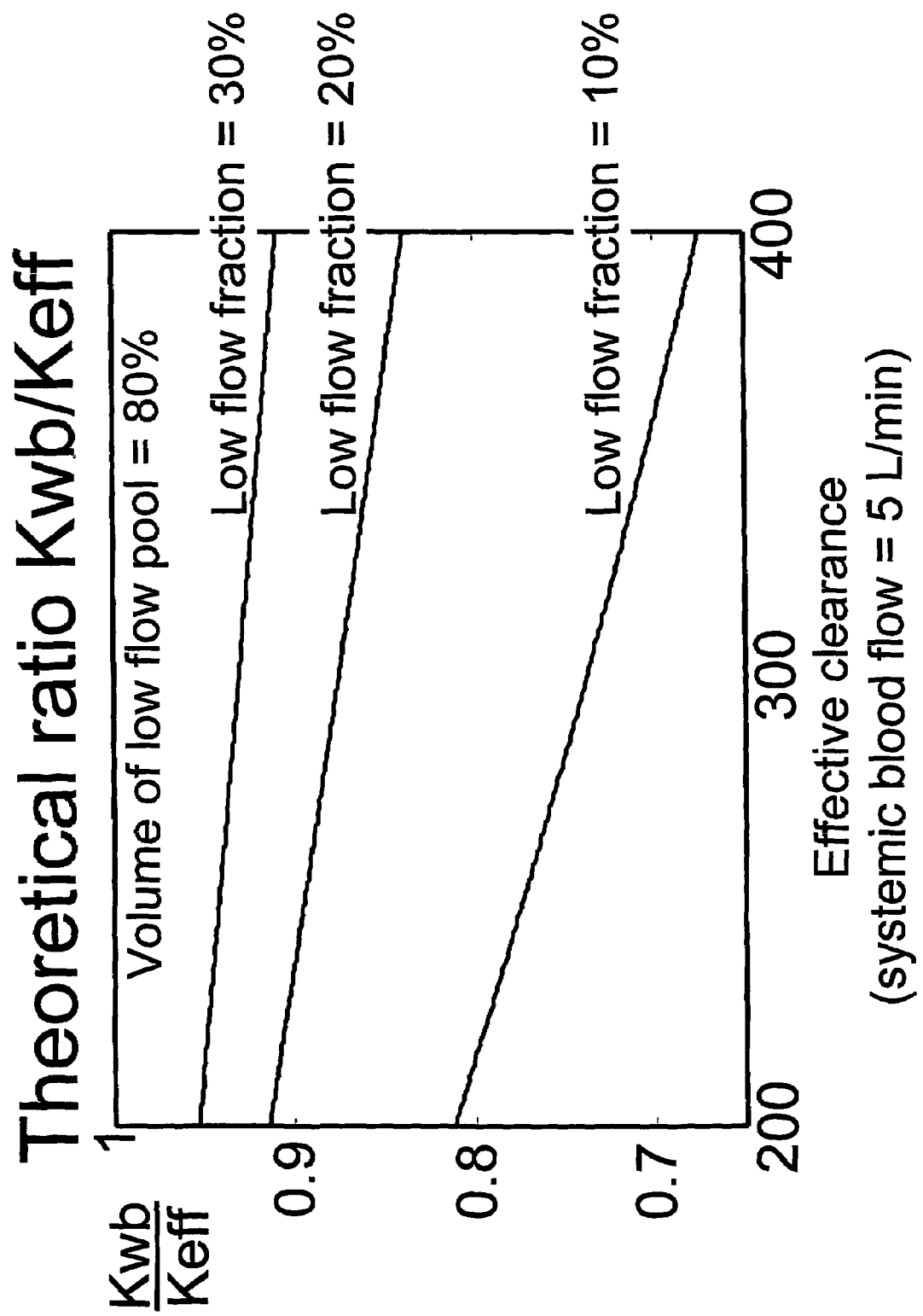

Referring to FIG. 24. Shown here is the theoretical clearance ratio as a function of the effective clearance for a systemic blood flow of 5 L/min, a low flow pool volume of 80% of the total volume, and a flow fraction to this pool of 10, 20 and 30% of the total systemic flow. This range of parameters agrees with what Daugirdas and Schneditz found necessary to explain observed urea rebound. In our study the clearances were slightly above 200, and we see that the theoretical ratio variation is between 0.8 and 0.95, which agrees well with the clinical results. We also see that at higher clearances between 300 and 400, whole body clearance can be as much as 30% or more below the effective clearance, but the actual ratio depends heavily on the patient parameters.

The following conclusions can be drawn. Effective clearance by conductivity overestimates whole body clearance in a patient dependent way. Last, but not least, in patients with a large gap between whole body clearance and effective clearance (i.e. a small ratio) there seems to be a large potential for efficiency improvements by affecting the patient parameters. The big question is how this could be achieved.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A method of estimating a process efficiency of a dialysis system comprising a dialyzer, wherein said dialyzer is connected to a patient's blood system for performing a dialysis treatment of a patient, said dialyzer having a potential clearance capacity ($K_{eff}$, K), wherein said method comprises:
using said dialyzer to determine a whole body clearance ratio ($K_{wb}/K_{eff}$, $K_{wb}/K$) value representing a whole body clearance of the patient divided by the potential clearance capacity ($K_{eff}$, K) of the dialyzer.

2. A method according to claim 1, wherein the step of determining the whole body clearance ratio ($K_{wb}/K_{eff}$, $K_{wb}/K$) value comprises:
measuring a final blood urea concentration no later than approximately one minute after the end of a dialysis treatment;
measuring an equilibrated blood urea concentration no earlier than approximately one half hour after the end of the dialysis treatment; and
dividing said final blood urea concentration by said equilibrated blood urea concentration so as to obtain the whole body clearance ratio value.

3. A method according to claim 2, wherein said measuring of said final blood urea concentration includes measuring said final blood urea concentration immediately after the end of the dialysis treatment.

4. A method according to claim 2, wherein said measuring of said final blood urea concentration includes measuring said final blood urea concentration approximately one minute after the end of the dialysis treatment.

5. A method according to claim 1, wherein the step of determining the whole body clearance ratio ($K_{wb}/K_{eff}$, $K_{wb}/K$) value comprises:
measuring an initial urea concentration ($C_{d0}$, $C_{b0}$);
measuring at least two subsequent urea concentration values at spaced time intervals after the dialysis treatment has started, a first value of said at least two values being measured no earlier than approximately one half hour after the dialysis treatment has started;

deriving a starting urea concentration based on an extrapolation in time of said at least two values back to the start of the dialysis treatment; and dividing said starting urea concentration by said initial urea concentration ($C_{d0}$, $C_{b0}$).

6. A method of estimating a whole body clearance ratio ($K_{wb}/K_{eff}$) value, with respect to an effective clearance ($K_{eff}$), of a dialysis treatment of a patient, said whole body clearance ratio ($K_{wb}/K_{eff}$) value defining a response by the patient to a potential clearance capacity ($K_{eff}$) of a dialyzer performing the dialysis treatment, comprising:

using said dialyzer to determine the whole body clearance ratio ($K_{wb}/K_{eff}$) value so as to represent a whole body clearance divided by an effective clearance of the dialysis treatment, the whole body clearance ratio value being based on a measurement of a slope ($K_{wb}/V$) of a logarithmic removal rate function ($C_d$, $C_b$), said function corresponding to a lowering of a urea concentration during the dialysis treatment.

7. A method according to claim 6, further comprising:

determining an initial dialysate urea concentration ($C_{d0}$);

determining a total flow rate ($Q_d$) of spent dialysate during the dialysis treatment, said dialysis treatment including any ultrafiltration;

calculating, based on measurements performed during a steady state phase ($t_3$-$t_4$) of the treatment, the slope ($K_{wb}/V$) of said logarithmic removal rate function ($C_d$);

measuring a predialysis urea mass ($m_0$); and determining the whole body clearance ratio ($K_{wb}/K_{eff}$) value as a product of said slope ($K_{wb}/V$) and said predialysis urea mass ($m_0$), divided by said total flow rate ($Q_d$) and divided by said initial dialysate urea concentration ($C_{d0}$).

8. A method according to claim 6, further comprising:

calculating, based on measurements performed during a steady state phase ($t_3$-$t_4$) of the dialysis treatment, the slope ($K_{wb}/V$) of said logarithmic removal rate function ($C_d$, $C_b$);

determining an entire distribution volume (V); and determining the whole body clearance ratio ($K_{wb}/K_{eff}$, $K_{wb}/K$) value as the product of said slope ($K_{wb}/V$) and said entire distribution volume (V) divided by the potential cleaning capacity ($K_{eff}$, K).

9. A method according to one of claims 7 or 8, wherein the slope ($K_{wb}/V$) of said logarithmic removal rate function ($C_d$) is measured on a dialysate side of a dialysis system comprising the dialyzer.

10. A method according to claim 8, wherein the slope ($K_{wb}/V$) of said logarithmic removal rate function ($C_b$) is measured on a blood side of a dialysis system comprising the dialyzer.

11. A method of performing a dialysis treatment program by a dialyzer, said method comprising the steps of:

performing a first dialysis treatment of the patient under a first set of conditions which include at least one of a treatment time and a composition of a dialysate in the dialyzer;

estimating, during the first dialysis treatment, a whole body clearance ratio ($K_{wb}/K_{eff}$, $K_{wb}/K$) value according to one of claims 2 to 6;

comparing the whole body clearance ratio ($K_{wb}/K_{eff}$, $K_{wb}/K$) value to a threshold ratio value; and performing a dialysis treatment of the patient after said first dialysis treatment under a second set of conditions which are different from the first set of conditions, if the whole body clearance ratio ($K_{wb}/K_{eff}$, $K_{wb}/K$) value is less than the threshold ratio value.

12. An apparatus comprising:

a urea monitor circuit configured to determine an initial dialysate urea concentration ($C_{d0}$), determine a total flow rate ($Q_d$) of spent dialysate during the dialysis treatment including any ultra filtration, measure, during a steady state phase ($t_3$-$t_4$) of the dialysis treatment, a slope ($K_{wb}/V$) of a removal rate function corresponding to a lowering of a dialysate urea concentration during the dialysis treatment, and measure a predialysis urea mass ($m_0$); and a processor configured to determine a whole body clearance ratio ($K_{wb}/K_{eff}$) value for the patient, said whole body clearance ratio ($K_{wb}/K_{eff}$) representing a whole body clearance of the patient divided by an effective clearance ($K_{eff}$), being determined as the product of said slope ($K_{wb}/V$) and said predialysis urea mass ($m_0$), divided by said flow rate ($Q_d$) and divided by said initial dialysate urea concentration ($C_{d0}$).

13. A computer-readable medium containing computer-executable instructions for performing a method of estimating a process efficiency of a dialysis system comprising a dialyzer, wherein the dialyzer is connected to a blood system of a patient for performing a dialysis treatment of the patient and the dialyzer has a potential clearance capacity, the computer-executable instructions comprising:

a set of computer-executable instructions for determining a whole body clearance ratio value representing a whole body clearance of the patient divided by the potential clearance capacity of the dialyzer.

14. A computer-readable medium according to claim 13, wherein said set of computer-executable instructions includes:

computer-executable instructions for receiving a final blood urea concentration measured no later than approximately one minute after the end of a dialysis treatment;

computer-executable instructions for receiving an equilibrated blood urea concentration measured no earlier than approximately one half hour after the end of the dialysis treatment;

computer-executable instructions for dividing said final blood urea concentration by said equilibrated blood urea concentration so as to obtain the whole body clearance ratio value; and computer-executable instructions for displaying the whole body clearance ratio value along with an indication that the whole body clearance ratio value is a whole body clearance ratio.

15. A computer-readable medium according to claim 13, wherein said set of computer-executable instructions includes:

computer-executable instructions for receiving an initial measured urea concentration;

computer-executable instructions for receiving at least two subsequent measured urea concentration values at spaced time intervals after the dialysis treatment has started, a first value of the at least two measured urea concentration values being measured no earlier than approximately one-half hour after the dialysis treatment has started;

computer-executable instructions for deriving a starting urea concentration based on an extrapolation in time of said at least two values back to the start of the dialysis treatment; and computer-executable instructions for dividing the starting urea concentration by the initial urea concentration.

16. A computer-readable medium according to claim 13, wherein said set of computer-executable instructions includes:
 computer-executable instructions for measuring a slope of a logarithmic removal rate function corresponding to a lowering of a urea concentration during the dialysis treatment; and
 computer-executable instructions for calculating the whole body clearance ratio value based on the slope of the logarithmic removal rate function.

17. A computer-readable medium according to claim 16, wherein said set of computer-executable instructions includes:
 computer-executable instructions for receiving an initial dialysate urea concentration;
 computer-executable instructions for receiving a total flow rate of spent dialysate during the dialysis treatment, the dialysis treatment including any ultrafiltration;
 computer-executable instructions for calculating, based on measurements performed during a steady state phase of the treatment, the slope of the logarithmic removal rate function;
 computer-executable instructions for receiving a predialysis urea mass; and
 computer-executable instructions for calculating the whole body clearance ratio value as a product of the slope and said predialysis urea mass, divided by the total flow rate and divided by the initial dialysate urea concentration.

18. A computer-readable medium according to claim 17, wherein said set of computer-executable instructions further includes computer-executable instructions for displaying the whole body clearance ratio value along with an indication that the whole body clearance ratio value is a whole body clearance ratio.

19. A computer-readable medium according to claim 16, wherein said set of computer-executable instructions includes:
 computer-executable instructions for calculating, based on measurements performed during a steady state phase of the dialysis treatment, the slope of said logarithmic removal rate function;
 computer-executable instructions for determining an entire distribution volume; and
 computer-executable instructions for determining the whole body clearance ratio value as the product of the slope and the entire distribution volume divided by the potential cleaning capacity.

* * * * *